US012109233B2

(12) United States Patent
Okazaki

(10) Patent No.: US 12,109,233 B2
(45) Date of Patent: Oct. 8, 2024

(54) PHARMACEUTICAL PREPARATION AND MEDICAL DEVICE

(71) Applicant: DR.C MEDICAL MEDICINE CO., LTD., Tokyo-to (JP)

(72) Inventor: Narumi Okazaki, Tokyo (JP)

(73) Assignee: DR.C MEDICAL MEDICINE CO., LTD., Tokyo-To (JP)

( * ) Notice: Subject to any disclaimer, the term of this patent is extended or adjusted under 35 U.S.C. 154(b) by 0 days.

(21) Appl. No.: 16/467,678

(22) PCT Filed: Dec. 21, 2016

(86) PCT No.: PCT/JP2016/088231
§ 371 (c)(1),
(2) Date: Jun. 7, 2019

(87) PCT Pub. No.: WO2018/105131
PCT Pub. Date: Jun. 14, 2018

(65) Prior Publication Data
US 2020/0069730 A1    Mar. 5, 2020

(30) Foreign Application Priority Data

Dec. 9, 2016   (JP) ................. 2016-239723

(51) Int. Cl.
*A61K 33/42*   (2006.01)
*A41D 13/11*   (2006.01)
*A61K 9/70*    (2006.01)
*A61K 33/24*   (2019.01)
*A61K 33/242*  (2019.01)
*A61K 33/243*  (2019.01)
*A61K 33/38*   (2006.01)

(52) U.S. Cl.
CPC .............. *A61K 33/42* (2013.01); *A41D 13/11* (2013.01); *A61K 9/70* (2013.01); *A61K 33/24* (2013.01); *A61K 33/242* (2019.01); *A61K 33/243* (2019.01); *A61K 33/38* (2013.01)

(58) Field of Classification Search
None
See application file for complete search history.

(56) References Cited

U.S. PATENT DOCUMENTS

| 2003/0125679 | A1 | 6/2003 | Kubota et al. | |
| 2006/0085027 | A1* | 4/2006 | Santin | A61F 5/56 606/199 |
| 2009/0252647 | A1* | 10/2009 | Orofino | A61L 2/18 422/28 |
| 2014/0044801 | A1 | 2/2014 | Sakurada et al. | |

FOREIGN PATENT DOCUMENTS

| JP | 2585946 | 2/1997 |
| JP | 10-277171 | 10/1998 |
| JP | 2963657 | 10/1999 |
| JP | 2001-178825 | 7/2001 |
| JP | 2013-181102 | 9/2013 |
| JP | 2014-40416 | 3/2014 |
| JP | 5995100 | 8/2016 |
| JP | 6011201 | 10/2016 |

OTHER PUBLICATIONS

Kasuga et al (Bactericidal activities of woven cotton and nonwoven polypropylene fabrics coated with hydroxyapatite-binding silver/titanium dioxide ceramic nanocomposite "Earth-plus". International Journal of Nanomedicine 2011:6 1937-1943 (Year: 2011).*
Fujitsu (https://journal.jp.fujitsu.com/en/2014/03/14/01/ (2014)) (Year: 2014).*
WebMD (https://www.webmd.com/allergies/news/20140320/could-nasal-filter-device-help-ease-allergies (2014) (Year: 2014).*
English translations of International Preliminary Report on Patentability and Written Opinion issued Jun. 20, 2019 in International Application (PCT) No. PCT/JP2016/088231.
Supplemental European Search Report issued Jun. 8, 2020 in corresponding European Patent Application No. 16923364.0.
International Search Report issued Feb. 7, 2017 in International Application No. PCT/JP2016/088231.
Written Opinion of the International Searching Authority issued Feb. 7, 2017 in International Application No. PCT/JP2016/088231, in Japanese language.
Request for International Application (replaced) issued Oct. 16, 2017 in International Application No. PCT/JP2016/088231.
Office Action issued Nov. 10, 2017 in Japanese patent application No. 2017-544978, with English translation.
Office Action issued Feb. 13, 2018 in Japanese patent application No. 2017-544978, with English translation.
Eriko Kasuga et al., "Bactericidal activities of woven cotton and nonwoven polypropylene fabrics coated with hydroxapatite-binding silver/titanium dioxide ceramic nanocomposite "Earth-plus"", International Journal of Nanomedicine, 2011:6, pp. 1937-1943.
Narumi Okazaki et al., "An Analysis of the Clinical Benefits of Hydroxyl Ag Titan Sheet (HATS) in 12 Adults with Hay Fever", Public Health Research 2016, 6(6):168-176, Scientific & Academic Publishing Co., Ltd.
Hydro Gin Titan de Gekiteki ni Kafunsho o Yobo!, Columbus, Oct. 2016, The November issue, pp. 20 to 22, partial English translation.

(Continued)

*Primary Examiner* — Jake M Vu

(74) *Attorney, Agent, or Firm* — Wenderoth, Lind & Ponack, L.L.P.

(57) ABSTRACT

A problem to be solved by the present invention is to provide a pharmaceutical preparation to be administered to the intranasal mucosa, and in order to solve such a problem, the present invention provides a pharmaceutical preparation to be administered to the intranasal mucosa, in which the pharmaceutical preparation includes a composite particle containing one or more titanium oxide particles, one or more metal particles, and one or more calcium phosphate particles.

9 Claims, 15 Drawing Sheets

(56) References Cited

OTHER PUBLICATIONS

Noboru Koyama et al., "Hikari Shokubai Titan Apatite no Allergen Fukatsuka Koka", Japanese Journal of Allergology, 2004, vol. 53, No. 2/3, p. 331, English translation.
Written Opinion of the International Searching Authority issued Feb. 7, 2017 in International Application No. PCT/JP2016/088231, English translation.
Office Action issued Feb. 25, 2021, in corresponding Chinese Patent Application No. 201680091434.4, with Machine English translation.
Office Action issued Dec. 9, 2021 in corresponding Chinese Patent Application No. 201680091434.4, with English Machine Translation.

\* cited by examiner (×10000)

(×3000)

(×5000)

(×5000)

(×5000)

(×5000)

PHARMACEUTICAL PREPARATION AND MEDICAL DEVICE

CROSS-REFERENCE TO RELATED APPLICATIONS

This application claims the priority of the Japanese Patent Application No. 2016-239723 filed on Dec. 9, 2016, the entire disclosure of which is incorporated herein by reference.

BACKGROUND OF THE INVENTION

Field of the Invention

The present invention relates to a pharmaceutical preparation to be administered to an intranasal mucosa, a medical device for preventing or treating rhinitis, a method for preventing or treating rhinitis, a composite particle for use in a method for preventing or treating rhinitis, and use of a composite particle for manufacturing a pharmaceutical preparation for preventing or treating rhinitis.

Background Art

Allergic rhinitis is a disease which is initiated by the reaction of the autoimmune system in the body to causative agents in the external environment, and house dust, mites, mold, pollen, and the like are known as causative agents.

As methods of treatment of allergic rhinitis, medical agent therapy, hyposensitization therapy, and the like are known.

For medical agent therapy, steroidal antiinflammatory agents, immunosuppressive agents, antihistaminic agents, and the like are used, but there is a fear that these medical agents may cause side effects. As the side effects of steroidal antiinflammatory agents, for example, side effects such as adrenal atrophy, dysfunction, and gastric ulcer are known, and as the side effects of immunosuppressive agents, for example, side effects such as infectious diseases are known, and as the side effects of antihistaminic agents, for example, side effects such as malaise, drowsiness, and vertigo are known.

Hyposensitization therapy is a method in which an antigen related to allergy is identified and hyposensitization is induced by administering the antigen intradermally, thereby inhibiting only the immunoreaction specific to the necessary antigen, but the therapy usually requires a few months to several years to exhibit sufficient effects. There is also a risk such as anaphylactic shock caused by direct systemic administration of an antigen responsible for allergy, and the dose needs to be increased gradually from a small amount. In addition, hyposensitization therapy not only requires a long-term treatment but also involves a patient's discomfort due to injection.

Non-Patent Document 1 describes the "Earthplus™" manufactured and sold by Shinshu Ceramics Co., Ltd. (Nagano Prefecture, Japan) as having bactericidal property against *Staphylococcus aureus, Escherichia coli*, and *Pseudomonas aeruginosa*. The earthplus is a powder of a composite material into which titanium oxide, silver, and hydroxyapatite are composited, and contains composite particles including one or more titanium oxide particles, one or more silver particles, and one or more hydroxyapatite particles. In the composite particle, one or more titanium oxide particles, one or more silver particles, and one or more hydroxyapatite particles are arranged three-dimensionally and randomly, and at least one silver particle is fixedly attached to at least one titanium oxide particle. The earthplus exerts a bactericidal action on the basis of the photocatalytic action of titanium oxide particles, the bactericidal action of silver particles, and the adsorbent action of hydroxyapatite particles. In other words, the earthplus adsorbs microorganisms by the adsorbent action of hydroxyapatite particles and exerts a bactericidal action against the microorganisms by the photocatalytic action of titanium oxide particles and the bactericidal action of silver particles.

The bactericidal action based on the photocatalytic action of the earthplus is considered to be exerted by the following mechanism. When the earthplus is radiated with ultraviolet rays (with a wavelength of 385 nm or less), electrons in the valence band which the titanium oxide particles have absorb energy for surpassing the band gap and are excited into the conduction band, generating positive holes (holes which have lost electrons) in the valence band. The excited electrons migrate to the silver particles bonded to the titanium oxide particles, thereby inhibiting rebonding between the excited electrons and the positive holes. The excited electrons effect reduction reaction on the surface of the titanium oxide particles and on the surface of the silver particles, and the positive holes effect oxidation reaction on the surface of the titanium oxide particles. For example, the excited electrons reduce oxygen to generate superoxide anions, and the positive holes oxidize moisture to generate hydroxyl radicals. It is considered that this active oxygen decomposes microorganisms, whereby a bactericidal action is exerted.

Patent Document 1 describes a functive obtained by thermally spraying, onto the surface of a substrate, composite ceramic composed of a powder mixture of an optical semiconductor ceramic (for example, titanium oxide), a metal (for example, silver) forming an electrode, and a ceramic (for example, hydroxyapatite) having an adsorbing function, and describes the functive as having bactericidal property against methicillin-resistant *Staphylococcus aureus* (MRSA).

Patent Document 2 describes an adherent treatment agent including a photocatalyst obtained by combining a semiconductor powder (for example, titanium oxide powder) with a metal powder (for example, silver powder), and including an adsorbing material (for example, hydroxyapatite) for adsorbing and retaining an object (for example, bacteria) to be treated by the photocatalytic action, and describes the adherent treatment agent as having bactericidal property against methicillin-resistant *Staphylococcus aureus* (MRSA) and *Pseudomonas aeruginosa*.

Patent Document 3 describes a mixture of metal-ceramic-bonded particles, in which metal particles (for example, silver particles) and ceramic particles (for example, titanium oxide particles) are bonded, and an adsorbing material (for example, hydroxyapatite), and describes the mixture as having bactericidal property against *Staphylococcus aureus* and *Escherichia coli* in the absence of light. In Patent Document 3, the metal-ceramic-bonded particles are manufactured by carrying out, to metal particles and ceramic particles, a step selected from the group consisting of (1) the step of passing them through a zone hold at high temperature, (2) the step of pressurizing them using a ball mill, and (3) the step of concurrently heating and pressurizing them using any one of a ball mill, a high temperature roller, and a high temperature ultrasonic crimping method.

PRIOR ART DOCUMENTS

Patent Documents

Patent Document 1: Japanese Patent No. 2585946
Patent Document 2: Japanese Patent No. 2963657
Patent Document 3: Japanese Patent No. 5995100

Non-Patent Document

Non-Patent Document 1: Eriko Kasuga et al., Bactericidal activities of woven cotton and nonwoven polypropylene fabrics coated with hydroxyapatite-binding silver/titanium dioxide ceramic noncomposite "Earth-plus", International Journal of Nanomedicine, 2011:6, pp.1937-1943

SUMMARY OF THE INVENTION

Technical Problem

An object of the present invention is to provide a pharmaceutical preparation to be administered to an intranasal mucosa, a medical device for preventing or treating rhinitis, a method for preventing or treating rhinitis, a composite particle for use in a method for preventing or treating rhinitis, and use of a composite particle for manufacturing a pharmaceutical preparation for preventing or treating rhinitis.

Solution to Problem

The present inventor has come to complete the present invention by finding out that composite particles including one or more titanium oxide particles, one or more metal particles, and one or more calcium phosphate particles can be administered to the intranasal mucosa of a subject in need of prevention or treatment of rhinitis, thereby preventing or treating the rhinitis of the subject. The composite particles exert the effect of prevention or treatment on rhinitis in a subject's nasal cavity where light necessary for expression of a photocatalytic action is not present, and this is a surprising finding which is unforeseeable from conventional findings.

According to one aspect of the present invention, the following pharmaceutical preparations are provided.

[A1] A pharmaceutical preparation to be administered to the intranasal mucosa, including a composite particle containing one or more titanium oxide particles, one or more metal particles, and one or more calcium phosphate particles.

[A2] The pharmaceutical preparation according to [A1], for preventing or treating rhinitis.

[A3] The pharmaceutical preparation according to [A2], wherein the rhinitis is allergic rhinitis.

[A4] The pharmaceutical preparation according to any one of [A1] to [A3], wherein, in the composite particle, the one or more titanium oxide particles, the one or more metal particles, and the one or more calcium phosphate particles are arranged three-dimensionally and randomly.

[A5] The pharmaceutical preparation according to any one of [A1] to [A4], wherein at least one metal particle of the one or more metal particles is fixedly attached to at least one titanium oxide particle of the one or more titanium oxide particles.

[A6] The pharmaceutical preparation according to any one of [A1] to [A5], wherein the one or more metal particles are selected from the group consisting of a silver particle, a gold particle, a platinum particle, and a copper particle.

[A7] The pharmaceutical preparation according to any one of [A1] to [A6], wherein the one or more metal particles include a silver particle, and the one or more calcium phosphate particles include a hydroxyapatite particle.

According to another aspect of the present invention, the following medical devices (hereinafter may be referred to as "first medical device") are provided.

[B1] A medical device for preventing or treating rhinitis, the medical device including a breathable mask portion covering the nostrils of a subject in need of prevention or treatment of rhinitis, an ear loop portion provided on the breathable mask portion, and a composite particle detachably attached to the breathable mask portion, wherein the composite particle includes one or more titanium oxide particles, one or more metal particles, and one or more calcium phosphate particles.

[B2] The medical device according to [B1], wherein the rhinitis is allergic rhinitis.

[B3] The medical device according to [B1] or [B2], wherein, in the composite particle, the one or more titanium oxide particles, the one or more metal particles, and the one or more calcium phosphate particles are arranged three-dimensionally and randomly.

[B4] The medical device according to any one of [B1] to [B3], wherein at least one metal particle of the one or more metal particles is fixedly attached to at least one titanium oxide particle of the one or more titanium oxide particles.

[B5] The medical device according to any one of [B1] to [B4], wherein the one or more metal particles are selected from the group consisting of a silver particle, a gold particle, a platinum particle, and a copper particle.

[B6] The medical device according to any one of [B1] to [B5], wherein the one or more metal particles include a silver particle, and the one or more calcium phosphate particles include a hydroxyapatite particle.

According to still another aspect of the present invention, the following medical devices (hereinafter may be referred to as "second medical device") are provided.

[C1] A medical device for preventing or treating rhinitis, which is inserted for use into the nasal cavity of a subject in need of prevention or treatment of rhinitis, the medical device including a sheet portion to be inserted into the nasal cavity of the subject and a composite particle attached to the sheet portion, wherein the composite particle includes one or more titanium oxide particles, one or more metal particles, and one or more calcium phosphate particles.

[C2] The medical device according to [C1], wherein the rhinitis is allergic rhinitis.

[C3] The medical device according to [C1] or [C2], wherein, in the composite particle, the one or more titanium oxide particles, the one or more metal particles, and the one or more calcium phosphate particles are arranged three-dimensionally and randomly.

[C4] The medical device according to any one of [C1] to [C3], wherein at least one metal particle of the one or more metal particles is fixedly attached to at least one titanium oxide particle of the one or more titanium oxide particles.

[C5] The medical device according to any one of [C1] to [C4], wherein the one or more metal particles are selected from the group consisting of a silver particle, a gold particle, a platinum particle, and a copper particle.

[C6] The medical device according to any one of [C1] to [C5], wherein the one or more metal particles include a silver particle, and the one or more calcium phosphate particles include a hydroxyapatite particle.

[C7] The medical device according to any one of [C1] to [C6], wherein the sheet portion is breathable.

[C8] The medical device according to any one of [C1] to [C7], wherein the composite particle is detachably attached to the sheet portion.

According to still another aspect of the present invention, the following methods are provided.

[D1] A method for preventing or treating rhinitis, the method includes the step of administering a composite particle to the intranasal mucosa of a subject in need of prevention or treatment of rhinitis, wherein the composite particle includes one or more titanium oxide particles, one or more metal particles, and one or more calcium phosphate particles.

[D2] The method according to [D1], wherein the rhinitis is allergic rhinitis.

[D3] The method according to [D1] or [D2], wherein, in the composite particle, the one or more titanium oxide particles, the one or more metal particles, and the one or more calcium phosphate particles are arranged three-dimensionally and randomly.

[D4] The method according to any one of [D1] to [D3], wherein at least one metal particle of the one or more metal particles is fixedly attached to at least one titanium oxide particle of the one or more titanium oxide particles.

[D5] The method according to any one of [D1] to [D4], wherein the one or more metal particles are selected from the group consisting of a silver particle, a gold particle, a platinum particle, and a copper particle.

[D6] The method according to any one of [D1] to [D5], wherein the one or more metal particles include a silver particle, and the one or more calcium phosphate particles include a hydroxyapatite particle.

[D7] The method according to any one of [D1] to [D6], wherein, in the administration step, the composite particle is administered to the intranasal mucosa of the subject by administering the pharmaceutical preparation according to the present invention (in other words, the pharmaceutical preparation according to any one of [A1] to [A7]) to the intranasal mucosa.

[D8] The method according to any one of [D1] to [D6], wherein, in the administration step, the composite particle is administered to the intranasal mucosa of the subject by putting the first medical device (in other words, the medical device according to any one of [B1] to [B6]) on the face of the subject.

[D9] The method according to any one of [D1] to [D6], wherein, in the administration step, the composite particle is administered to the intranasal mucosa of the subject by inserting the second medical device (in other words, the medical device according to any one of [C1] to [C8]) into the nasal cavity of the subject.

According to still another aspect of the present invention, the following composite particles are provided.

[E1] A composite particle for use in a method for preventing or treating rhinitis, the composite particle including one or more titanium oxide particles, one or more metal particles, and one or more calcium phosphate particles.

[E2] The composite particle according to [E1], wherein the rhinitis is allergic rhinitis.

[E3] The composite particle according to [E1] or [E2], wherein, in the composite particle, the one or more titanium oxide particles, the one or more metal particles, and the one or more calcium phosphate particles are arranged three-dimensionally and randomly.

[E4] The composite particle according to any one of [E1] to [E3], wherein at least one metal particle of the one or more metal particles is fixedly attached to at least one titanium oxide particle of the one or more titanium oxide particles.

[E5] The composite particle according to any one of [E1] to [E4], wherein the one or more metal particles are selected from the group consisting of a silver particle, a gold particle, a platinum particle, and a copper particle.

[E6] The composite particle according to any one of [E1] to [E5], wherein the one or more metal particles include a silver particle, and the one or more calcium phosphate particles include a hydroxyapatite particle.

[E7] The composite particle according to any one of [E1] to [E6], wherein, in the method, the composite particle is administered to the intranasal mucosa.

According to still another aspect of the present invention, the following uses are provided.

[F1] A use of a composite particle for manufacturing a pharmaceutical preparation for preventing or treating rhinitis, the composite particle including one or more titanium oxide particles, one or more metal particles, and one or more calcium phosphate particles.

[F2] The use according to [F1], wherein the rhinitis is allergic rhinitis.

[F3] The use according to [F1] or [F2], wherein, in the composite particle, the one or more titanium oxide particles, the one or more metal particles, and the one or more calcium phosphate particles are arranged three-dimensionally and randomly.

[F4] The use according to any one of [F1] to [F3], wherein at least one metal particle of the one or more metal particles is fixedly attached to at least one titanium oxide particle of the one or more titanium oxide particles.

[F5] The use according to any one of [F1] to [F4], wherein the one or more metal particles are selected from the group consisting of a silver particle, a gold particle, a platinum particle, and a copper particle.

[F6] The use according to any one of [F1] to [F5], wherein the one or more metal particles include a silver particle, and the one or more calcium phosphate particles include a hydroxyapatite particle.

Advantageous Effects of Invention

According to the present invention, pharmaceutical preparations to be administered to the intranasal mucosa, medical devices for preventing or treating rhinitis, methods for preventing or treating rhinitis, composite particles for use in methods for preventing or treating rhinitis, and uses of composite particles for manufacturing pharmaceutical preparations for preventing or treating rhinitis are provided.

DETAILED DESCRIPTION OF THE INVENTION

Figure 1:
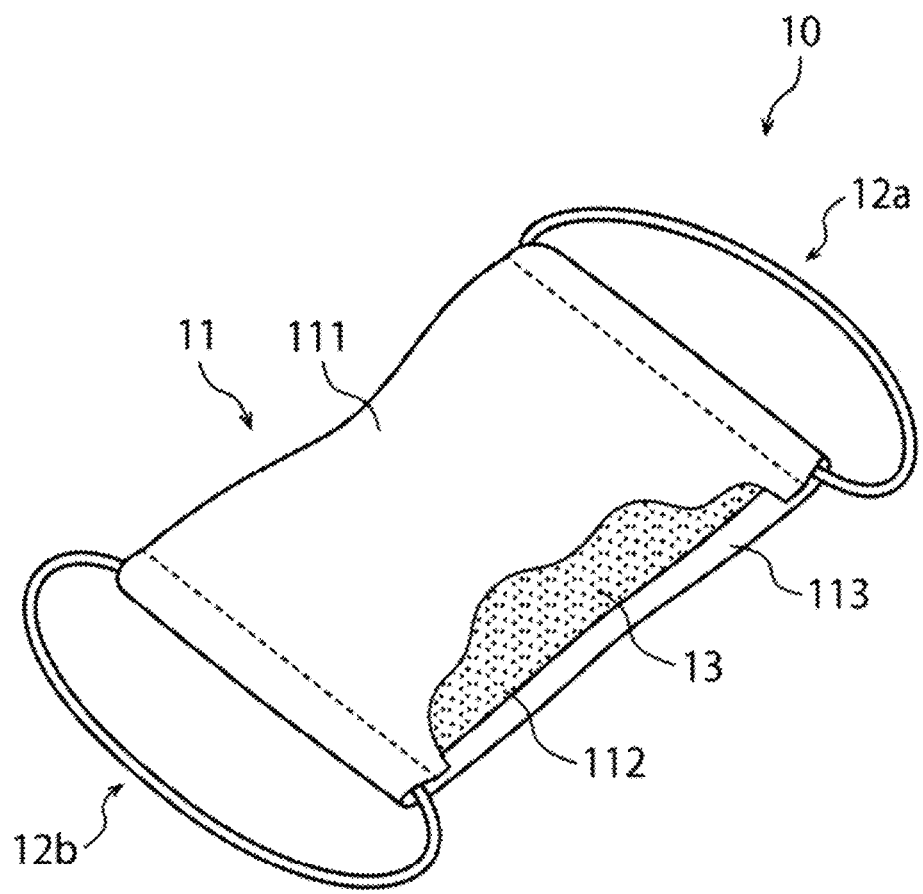
FIG. 1 is a partially cutaway view illustrating one embodiment of a first medical device according to the present invention.

Below, the present invention will be described in detail.
Composite Particle

The following description about a composite particle applies to any aspect encompassed in the present invention, unless otherwise specified.

The composite particle used in the present invention includes one or more titanium oxide particles, one or more metal particles, and one or more calcium phosphate particles.

The number of titanium oxide particles per composite particle may be one or may be two or more. The number of titanium oxide particles per composite particle is usually two or more.

Examples of forms of the titanium oxide particle included in the composite particle include, for example, a globular, granular, acicular, flaky, amorphous, or other form, but are not particularly limited thereto. The composite particle may include two or more titanium oxide particles having different forms.

The particle size of the titanium oxide particle included in the composite particle can be adjusted, if appropriate, depending on the particle size of the composite particle and is not limited to a particular size as long as it is smaller than the particle size of the composite particle. The titanium oxide particle included in the composite particle is, for example, a nanoparticle or a submicron particle.

Examples of crystal structures of the titanium oxide constituting the titanium oxide particle include, for example, an anatase type, rutile type, brookite type, and the like, and among these, an anatase type is preferable.

The number of metal particles per composite particle may be one or may be two or more. The number of metal particles per composite particle is usually two or more.

Examples of forms of the metal particle included in the composite particle include, for example, a globular, granular, acicular, flaky, amorphous, or other form, but are not particularly limited thereto. The composite particle may include two or more metal particles having different forms.

The particle size of the metal particle included in the composite particle can be adjusted, if appropriate, depending on the particle size of the composite particle and is not limited to a particular size as long as it is smaller than the particle size of the composite particle. The metal particle included in the composite particle is, for example, a nanoparticle or a submicron particle.

The metal particle included in the composite particle is, for example, selected from the group consisting of a silver particle, a gold particle, a platinum particle, and a copper particle. The metal particle included in the composite particle is preferably a silver particle. The composite particle may include two or more metal particles of different species.

The number of calcium phosphate particles per composite particle may be one or may be two or more. The number of calcium phosphate particles per composite particle is usually two or more.

Examples of forms of the calcium phosphate particle included in the composite particle include, for example, a globular, granular, acicular, flaky, amorphous, or other form, but are not particularly limited thereto. The composite particle may include two or more calcium phosphate particles having different forms.

The particle size of the calcium phosphate particle included in the composite particle can be adjusted, if appropriate, depending on the particle size of the composite particle and is not limited to a particular size as long as it is smaller than the particle size of the composite particle. The calcium phosphate particle included in the composite particle is, for example, a nanoparticle or a submicron particle.

Examples of calcium phosphates constituting the calcium phosphate particle include, for example, apatite, tricalcium phosphate, octacalcium phosphate, and the like, and among these, apatite is preferable. Examples of apatites include, for example, hydroxyapatite, apatite fluoride, carbonate apatite, and the like, and among these, hydroxyapatite ($Ca_{10}(PO_4)_6(OH)_2$) is preferable.

The content of titanium oxide particles, metal particles, and calcium phosphate particles per composite particle is not limited to a particular value, but the lower limit value of the titanium oxide particle content is usually 10 parts by mass, preferably 20 parts by mass, more preferably 25 parts by mass, still more preferably 30 parts by mass, relative to 1 part by mass of metal particles, and the upper limit value of the titanium oxide particle content is usually 300 parts by mass, preferably 250 parts by mass, more preferably 200 parts by mass, still more preferably 180 parts by mass, relative to 1 part by mass of metal particles. The lower limit value of the calcium phosphate particle content is usually 1 part by mass, preferably 2 parts by mass, more preferably 3 parts by mass, relative to 1 part by mass of metal particles, and the upper limit value of the calcium phosphate particle content is usually 100 parts by mass, preferably 80 parts by mass, more preferably 60 parts by mass, still more preferably 50 parts by mass.

The particle size of the composite particle as measured by dynamic light scattering is preferably 100 to 600 nm, more preferably 200 to 500 nm, still more preferably 250 to 350 nm. A particle size measurement by dynamic light scattering is made by a commercially available dynamic light scattering type particle size distribution measuring device, preferably the dynamic light scattering type nano tracking particle size distribution measuring device, "UPA-EX150" (made by Nikkiso Co., Ltd.)

In the composite particle, one or more titanium oxide particles, one or more metal particles, and one or more calcium phosphate particles are preferably arranged three-dimensionally and randomly.

In one embodiment of the three-dimensional and random arrangement, at least one metal particle is fixedly attached to at least one titanium oxide particle.

In one embodiment of the three-dimensional and random arrangement, one or more particles (one or more particles selected from a titanium oxide particle, a metal particle, or a calcium phosphate particle) are present around another particle (one particle selected from a titanium oxide particle, a metal particle, or a calcium phosphate particle). In this embodiment, one or more particles of the same species may be adjacent to a particle, and one or more particles of different species may be adjacent to a particle. The adjacent particles are preferably bonded and fixedly attached to one another. Examples of combinations of adjacent particles include a combination between titanium oxide particles, between metal particles, between calcium phosphate particles, between a titanium oxide particle and a metal particle, between a titanium oxide particle and a calcium phosphate particle, between a metal particle and a calcium phosphate particle, and the like.

In one embodiment of the three-dimensional and random arrangement, part of at least one particle selected from a titanium oxide particle, a metal particle or a calcium phosphate particle is exposed at the surface of the composite particle.

In one embodiment of the three-dimensional and random arrangement, part of at least one titanium oxide particle, part of at least one metal particle, and part of at least one calcium phosphate particle are exposed at the surface of the composite particle.

In one embodiment of the three-dimensional and random arrangement, at least one particle selected from a titanium oxide particle, a metal particle, or a calcium phosphate particle is present within the composite particle without being exposed at the surface of the composite particle.

In one embodiment of the three-dimensional and random arrangement, at least one particle selected from a titanium oxide particle, a metal particle, or a calcium phosphate particle has a membranous form and is present at at least part of the surface of the composite particle.

In one embodiment of the three-dimensional and random arrangement, two or more particles selected from a titanium oxide particle, a metal particle, or a calcium phosphate particle are formed in one piece or in a row, having a membranous form, and are present at at least part of the surface of the composite particle.

Whether a particle has a particulate form, has a membranous form, or forms a membranous form in one piece or in a row together with one or more of other particles is influenced by the compounding ratios of particles in the manufacture of the composite particles, and the like. Depending on the compounding ratio, a particle may no longer maintain a particulate form but may take a membranous form present at at least part of the surface of the composite particle. For example, in a case in which particles are composited by a mechanical approach such as bead mill and ball mill, a particle (for example, silver particle) composed of a material having a lower hardness than other particles may take such a membranous form.

Two or more of the aforementioned embodiments about the three-dimensional and random arrangement may be combined.

As the composite particle, for example, a composite material powder available from Shinshu Ceramics Co., Ltd. under the trade name of "earthplus" can be used. The earthplus is a powder of a composite material into which titanium oxide, silver, and hydroxyapatite are composited, and contains a composite particle including one or more titanium oxide particles, one or more silver particles, and one or more hydroxyapatite particles. In the composite particle, one or more titanium oxide particles, one or more silver particles, and one or more hydroxyapatite particles are arranged three-dimensionally and randomly, and at least one silver particle is fixedly attached to at least one titanium oxide particle. In the composite particle, part of at least one titanium oxide particle, part of at least one silver particle, and part of at least one hydroxyapatite particle are considered to be exposed at the surface of the composite particle.

The composite particle can be manufactured, for example, by using a wet mill to mix titanium oxide powder, metal powder, and calcium phosphate powder in a liquid and compositing one or more titanium oxide particles included in the titanium oxide powder, one or more metal particles included in the metal powder, and one or more calcium phosphate particles included in the calcium phosphate powder. The composite particle thus manufactured is used in the present invention without being sintered.

The content (purity) of titanium oxide in the titanium oxide powder is preferably 90% by weight or more, more preferably 95% by weight or more, still more preferably 98% or more. The upper limit value is, for example, 99%.

The particle size of the titanium oxide particle (primary particle) included in the titanium oxide powder is, for example, 0.03 to 0.1 μm, but is not particularly limited thereto. Because wet mills can make a particle aggregate into individual dispersed particles, the titanium oxide powder may include an aggregate (secondary particle) of titanium oxide particles. The particle size of an aggregate of titanium oxide particles is, for example, 1 to 2 μm. The particle size of a titanium oxide particle or an aggregate thereof is measured, for example, using a transmission electron microscope (TEM) or a scanning electron microscope (SEM).

The metal content (purity) of the metal powder is preferably 80% by weight or more, more preferably 95% by weight or more, still more preferably 98% or more. The upper limit value is, for example, 99.9%.

The particle size of the metal particle (primary particle) included in the metal powder is, for example, 1.1 to 1.9 μm, but is not particularly limited thereto. Because wet mills can make a particle aggregate into individual dispersed particles, the metal powder may include an aggregate (secondary particle) of metal particles. Keeping a metal powder refrigerated until it is used can inhibit the aggregation of metal particles included in the metal powder. The particle size of a metal particle or an aggregate thereof is calculated, for example, on the basis on the specific surface area.

The calcium phosphate content (purity) of the calcium phosphate powder is preferably 90% by weight or more, more preferably 95% by weight or more, still more preferably 98% or more.

The particle size of the calcium phosphate particle (primary particle) included in the calcium phosphate powder is, for example, 0.1 to 0.2 μm, but is not particularly limited thereto. Because wet mills can make a particle aggregate into individual dispersed particles, the calcium phosphate powder may include an aggregate (secondary particle) of calcium phosphate particles. The particle size of an aggregate of calcium phosphate particles is, for example, 4 to 5 μm. The particle size of a calcium phosphate particle or an aggregate thereof is measured by, for example, a laser diffraction/scattering method.

Wet mills can composite one or more titanium oxide particles, one or more metal particles, and one or more calcium phosphate particles while dispersing and pulverizing, in a liquid, particles included in titanium oxide powder, metal powder, and calcium phosphate powder. Examples of wet mills include, for example, bead mills, ball mills, and the like, and among these, bead mills are preferable. Examples of materials of pulverizing media, such as beads and balls, to be used in mills such as bead mills and ball mills include, for example, alumina, zircon, zirconia, steel, glass, and the like, and among these, zirconia is preferable. The size (diameter) of pulverizing media can be adjusted, if appropriate, depending on the particle size of a composite particle to be manufactured, and the like, and is usually 0.05 to 3.0 mm, preferably 0.1 to 0.5 mm. As pulverizing media, for example, beads or balls having a size of about 0.1 mm and a mass of about 0.004 mg can be used.

Liquid used in mixing is, for example, an aqueous medium such as water. In a case in which liquid used in mixing is water, the total compounding amount of titanium oxide powder, metal powder, and calcium phosphate powder is adjusted in such a manner as to be usually 25 to 45 parts by mass, preferably 30 to 40 parts by mass, relative to 65 parts by mass of water.

When raw materials including titanium oxide powder, metal powder, calcium phosphate powder, and liquid are mixed in a wet mill, various conditions, for example, the total addition amount of raw material powders, the flow rate of the liquid, the circumferential speed of the blades within the cylinder, the stirring temperature, the stirring time, and the like can be adjusted, if appropriate, depending on the particle size of a composite particle to be manufactured, and the like. The total addition amount of raw material powders (titanium oxide powder, metal powder, and calcium phosphate powder) is, for example, 4 kg or more, the cylinder volume is, for example, 0.5 to 4 L, the flow rate of the liquid is, for example, 0.5 to 3 L/minute, the circumferential speed of the blade is, for example, 300 to 900 m/minute, the liquid temperature is, for example, 20 to 60° C., and the mixing time per 1 kg of raw material powder is, for example, 0.5 to 2 hours. The upper limit value of the total addition amount of raw material powders can be adjusted, if appropriate, depending on the cylinder volume and the like. The mixing time can be adjusted, if appropriate, depending on the total addition amount of raw material powders, and the like.

In addition to titanium oxide powder, metal powder, calcium phosphate powder, and liquid, a dispersant is preferably added to the raw materials. Examples of dispersants include, for example, a high molecular weight type dispersant, a low molecular weight type dispersant, an inorganic type dispersant, and the like, and a selection can be made, if appropriate, depending on the kind of liquid used in wet mixing. In a case in which liquid used in mixing is an aqueous medium such as water, for example, an anionic high molecular weight type dispersant, a nonionic high molecular weight type dispersant, or the like can be used as a dispersant; examples of anionic high molecular weight type dispersants include, for example, a polycarboxylic acid type dispersant, a formalin naphthalenesulfonate condensate type dispersant, and the like; and examples of nonionic high molecular weight type dispersants include for example, polyethylene glycol and the like. The addition amount of dispersant may be adjusted if appropriate, and is, for example, 0.1 to 3% by mass, preferably 0.3 to 1% by mass, relative to 35 parts by mass of the total compounding amount of titanium oxide powder, metal powder, and calcium phosphate powder A suspension (slurry) of composite particles can be manufactured by using a wet mill to mix titanium oxide powder, metal powder, and calcium phosphate powder in a liquid and compositing one or more titanium oxide particles included in the titanium oxide powder, one or more metal particles included in the metal powder, and one or more calcium phosphate particles included in the calcium phosphate powder. The solvent in the suspension is subsequently removed by evaporation or the like, whereby an assembled product (dry powder) of composite particles can be manufactured. An assembled product (dry powder) of composite particles can also be manufactured from a suspension (slurry) of composite particles by a known granulation method such as spray dry granulation.

The particle size of an assembled product of composite particles, as measured by dynamic light scattering, is, for example, 100 to 600 nm, preferably 200 to 500 nm. The median diameter (d50) of an assembled product of composite particles, as measured by dynamic light scattering on a volumetric basis, is, for example, 250 to 350 nm, preferably 300 nm. A particle size by dynamic light scattering is measured using a commercially available dynamic light scattering type particle size distribution measuring device, preferably the dynamic light scattering type nano tracking particle size distribution measuring device, "UPA-EX150" (made by Nikkiso Co., Ltd.)

The manufactured composite particles can be used in the present invention as they are, and the particle size may be adjusted before being used in the present invention. The adjustment of particle size can be carried out, for example, by sieving composite particles in the powder state or in the suspension state.

In the assembled product of composite particles, the respective numbers of titanium oxide particles, metal particles, and calcium phosphate particles per composite particle may be identical or different among the composite particles.

In addition to the composite particles including one or more titanium oxide particle, one or more metal particle, and one or more calcium phosphate particle, other particles which may be produced as byproducts in the manufacture of the composite particles may coexist in the assembled product of composite particles. Examples of other particles include, for example, an independent titanium oxide particle, an independent metal particle, an independent calcium phosphate particle, a bonded product of titanium oxide particles (including no metal particle and no calcium phosphate particle), a bonded product of metal particles (including no titanium oxide particle and no calcium phosphate particle), a bonded product of calcium phosphate particles (including no titanium oxide particle and no metal particle), a bonded product of a titanium oxide particle and a metal particle (including no calcium phosphate particle), a bonded product of a titanium oxide particle and a calcium phosphate particle (including no metal particle), a bonded product of a metal particle and a calcium phosphate particle (including no titanium oxide particle), and the like.

The composite particles can be used in methods for preventing or treating rhinitis, as described below. Accordingly, the present invention encompasses composite particles for use in methods for preventing or treating rhinitis.

The composite particles can be used to manufacture pharmaceutical preparations for preventing or treating rhinitis, as described below. Accordingly, the present invention encompasses uses of composite particles to manufacture pharmaceutical preparations for preventing or treating rhinitis.

Pharmaceutical Preparation

A pharmaceutical preparation according to the present invention is a pharmaceutical preparation to be administered to the intranasal mucosa, and includes composite particles containing one or more titanium oxide particles, one or more calcium phosphate particles, and one or more metal particles. To the composite particles, the aforementioned description applies.

The pharmaceutical preparation according to the present invention can be administered to the intranasal mucosa of a subject in need of prevention or treatment of rhinitis, thereby preventing or treating the rhinitis of the subject. The prevention of rhinitis includes preventing symptoms such as sneezing, nasal discharge, and nasal congestion which may occur in a subject in the future, and the treatment of rhinitis includes improving or inhibiting symptoms such as sneezing, nasal discharge, and nasal congestion which have already occurred in a subject.

Rhinitis to which the pharmaceutical preparation according to the present invention is applied is not limited to a particular symptom as long as they has inflammation occurring to the nasal mucosa and has a symptom such as sneezing, nasal discharge, or nasal congestion. The pharmaceutical preparation according to the present invention can be applied to various rhinitides.

Examples of rhinitides to which the pharmaceutical preparation according to the present invention is applied include, for example, infectious rhinitis, hypersensitive non-infectious rhinitis, stimulatory rhinitis, atrophic rhinitis, specific granulomatous rhinitis, and the like. Rhinitis to which the pharmaceutical preparation according to the present invention is applied is preferably infectious rhinitis, hypersensitive non-infectious rhinitis, and the like. Examples of infectious rhinitides include, for example, acute rhinitis, chronic rhinitis, and the like. Examples of hypersensitive non-infectious rhinitides include combined rhinitides (nasal hypersensitivity) such as allergic rhinitis and nonallergic rhinitis; rhinorrhea rhinitides such as gustatory rhinitis, cold-air inhalation rhinitis, and senile rhinitis; congestion rhinitides such as drug-induced rhinitis, psychogenic rhinitis, gestational rhinitis, endocrine rhinitis, and cold-induced rhinitis; dry rhinitis; and the like.

Rhinitis to which the pharmaceutical preparation according to the present invention is applied is preferably hypersensitive non-infectious rhinitis, more preferably allergic rhinitis or nonallergic rhinitis, still more preferably, allergic rhinitis.

Allergic rhinitides can be classified into perennial allergic rhinitis and seasonal allergic rhinitis in accordance with the predilection time. Allergic rhinitis to which the pharmaceutical preparation according to the present invention is applied may be perennial allergic rhinitis or seasonal allergic rhinitis. The pharmaceutical preparation according to the present invention can exert an excellent prevention or treatment effect on allergic rhinitides which have been considered difficult to prevent or treat, particularly perennial allergic rhinitis caused by house dust, mites, mold, and the like.

Allergic rhinitis is one kind of combined rhinitis (nasal hypersensitivity) in which two or more kinds of symptoms which are usually sneezing, aqueous rhinorrhea, and nasal congestion (snuffles) are combined, for example, sneezing and aqueous rhinorrhea are combined, or sneezing, aqueous rhinorrhea, and nasal congestion are combined. Allergic rhinitis is initiated by the reaction of the autoimmune system in the body to causative agents in the external environment. Examples of causative agents for allergic rhinitis include, for example, house dust, mites, mold, pollen, grass, trees, animals, and the like. More specifically, allergic rhinitis is a type I allergic disease of nasal mucosa, and is characterized by paroxysmal and recurrent sneezing, aqueous rhinorrhea, and nasal congestion, in principle. Because allergic rhinitis is a type I allergic disease, a patient with allergic rhinitis may have an allergic predisposition (anamnesis, complication, and family history of allergy) and may present the characteristics of increased serum specific IgE antibody level, increased local mast cells and eosinophils, nonspecific hypersensitive accentuation of mucosa, and the like. Out of allergic rhinitides, perennial allergic rhinitis is often caused by house dust or mites, and seasonal allergic rhinitis is often caused by pollen.

Rhinitis to which the pharmaceutical preparation according to the present invention is applied may be stimulatory rhinitis such as physical rhinitis, chemical rhinitis, or radiation rhinitis; and another rhinitis such as atrophic rhinitis or specific granulomatous rhinitis.

A subject to whom the pharmaceutical preparation according to the present invention is administered is usually a patient with rhinitis, preferably a patient with allergic rhinitis, but is not particularly limited thereto as long as the subject is in need of prevention or treatment of rhinitis.

A dose of the pharmaceutical preparation according to the present invention is an amount effective for prevention or treatment of rhinitis. The amount effective for prevention or treatment of rhinitis can be adjusted, if appropriate, depending on the dosage form of the pharmaceutical preparation, the degree of rhinitis, the dosage regimen, and the like. A dose of the pharmaceutical preparation according to the present invention for each time is adjusted so that the amount of the composite particles administered each time will be usually 0.1 to 10 µg, preferably 0.2 to 5 µg, more preferably 0.4 to 4 µg. The frequency of administration per day for the pharmaceutical preparation according to the present invention is usually 1 to 5 times, preferably 1 to 3 times, more preferably 1 to 2 times, but is not particularly limited thereto. The administration interval of the pharmaceutical preparation according to the present invention can be adjusted, if appropriate, taking into account the duration of the effect of prevention or treatment of rhinitis, and the like. In a case in which the pharmaceutical preparation according to the present invention has been administered to a subject in a period of one day on the basis of the aforementioned dose for each time and the aforementioned frequency of administration per day, the expected duration of the effect of prevention or treatment of rhinitis is usually from a few hours to several days, although there are differences between individual subjects, and in a case in which the pharmaceutical preparation according to the present invention has been administered to a subject in a period of one to two weeks on the basis of the aforementioned dose for each time and the aforementioned frequency of administration per day, the expected duration of the effect of prevention or treatment of rhinitis is usually from one week to two months, although there are differences between individual subjects.

The pharmaceutical preparation according to the present invention can be manufactured with a pharmaceutically acceptable additive compounded thereinto in addition to composite particles which are effective ingredients. Examples of such additives include, for example, pH adjustors, preservatives, flavoring agents, dispersants, wetting agents, stabilizers, antiseptics, suspensions, surfactants, and the like.

As a pH adjustor, one which is selected as appropriate from those generally used for external preparations can be used. The compounding amount of the pH adjustor can be adjusted, if appropriate, depending on the dosage form, the base ingredient, and the like. Examples of pH adjustors include, for example, inorganic acids such as hydrochloric acid, sulfuric acid, nitric acid, hydrobromic acid, and phosphoric acid; organic acids such as acetic acid, succinic acid, fumaric acid, malic acid, oxalic acid, lactic acid, glutaric acid, salicylic acid, and tartaric acid; salts of these acids; and the like. The pH adjustors may be used singly or in combination of two or more species thereof.

As a preservative, one which is selected as appropriate from those generally used for external preparations can be used. The compounding amount of the preservative can be adjusted, if appropriate, depending on the dosage form, the base ingredient, and the like. Examples of preservatives include, for example, parahydroxybenzoic acid, methylparaben, ethylparaben, propylparaben, chlorobutanol, benzyl alcohol, parahydroxybenzoic acid alkyl esters such as parahydroxybenzoic acid methyl and parahydroxybenzoic acid propyl, and the like The preservatives may be used singly or in combination of two or more species thereof.

As a flavoring agent, one which is selected as appropriate from those generally used for external preparations can be used. The compounding amount of the flavoring agent can be adjusted, if appropriate, depending on the dosage form, the base ingredient, and the like. Examples of flavoring agents include, for example, menthol, rose oil, eucalyptus oil, d-camphor, and the like. The flavoring agents may be used singly or in combination of two or more species thereof.

As a dispersant, one which is selected as appropriate from those generally used for external preparations can be used. The compounding amount of the dispersant can be adjusted, if appropriate, depending on the dosage form, the base ingredient, and the like. Examples of dispersants include, for example, sodium metaphosphate, calcium polyphosphate, silicic anhydride, and the like. The dispersants may be used singly or in combination of two or more species thereof.

As a wetting agent, one which is selected as appropriate from those generally used for external preparations can be used. The compounding amount of the wetting agent can be adjusted, if appropriate, depending on the dosage form, the base ingredient, and the like. Examples of wetting agents include, for example, propylene glycol, butylene glycol, glycerin, sorbitol, sodium lactate, sodium hyaluronate, and the like. The wetting agents may be used singly or in combination of two or more species thereof.

As a stabilizer, one which is selected as appropriate from those generally used for external preparations can be used. The compounding amount of the stabilizer can be adjusted, if appropriate, depending on the dosage form, the base ingredient, and the like. Examples of stabilizers include, for example, sodium bisulfite, tocopherol, ethylenediaminetetraacetic acid (EDTA), citric acid, and the like. The stabilizers may be used singly or in combination of two or more species thereof.

As an antiseptic, one which is selected as appropriate from those generally used for external preparations can be used. The compounding amount of the antiseptic can be adjusted, if appropriate, depending on the dosage form, the base ingredient, and the like. Examples of antiseptics include, for example, parahydroxybenzoic acid ethyl, parahydroxybenzoic acid propyl, benzalkonium hydrochloride, sorbic acid, and the like. The antiseptics may be used singly or in combination of two or more species thereof.

As a suspension, one which is selected as appropriate from those generally used for external preparations can be used. The compounding amount of the suspension can be adjusted, if appropriate, depending on the dosage form, the base ingredient, and the like. Examples of suspensions include, for example, powdered tragacanth, powdered acacia, bentonite, sodium carboxymethylcellulose, and the like. The suspensions may be used singly or in combination of two or more species thereof.

As a surfactant, one which is selected as appropriate from those generally used for external preparations can be used. The compounding amount of the surfactant can be adjusted, if appropriate, depending on the dosage form, the base ingredient, and the like. Examples of surfactants include, for example, polyoxyethylene hydrogenated castor oil, sorbitan fatty acid ester such as sorbitan sesquioleate, polyoxyl stearate, and the like. The surfactants may be used singly or in combination of two or more species thereof.

The dosage form of the pharmaceutical preparation according to the present invention is, for example, nasal drop, spray, aerosol, ointment, cream, lotion, liniment, cataplasm, plaster, patch, emplastrum, gel, liquid, tape, powder, granule, and the like, but is not particularly limited thereto as long as it can be administered to the intranasal mucosa. Formulation into a desired dosage form can be carried out using additives, bases, and the like suitable for each dosage form in accordance with a usual method set forth in the general rules for preparations of the Japanese Pharmacopoeia, and the like. Examples of substrates used in administration dosage form such as adhesive agent or tape include, for example, woven fabrics such as of cotton, staple fiber, cannabis, and chemical fiber; nonwoven fabrics such as of rayon, polyester, and nylon; plastic films such as of plasticized polyvinyl chloride, polyethylene, and polyurethane; and the like. The substrate may be a layered sheet composed of two or more layers.

In a case in which the dosage form is ointment or cream, for example, an oleaginous base or an emulsion base can be used as a base.

Examples of oleaginous bases include, for example, hydrocarbons, higher alcohol, higher fatty acid, higher fatty acid ester, glycol, vegetable oil, animal oil, and the like. The oleaginous bases may be used singly or in combination of two or more species thereof.

Examples of hydrocarbons usable as oleaginous bases include, for example, hydrocarbons having from 12 to 32 carbon atoms, and liquid paraffin, branched paraffin, solid paraffin, white petrolatum, yellow petrolatum, squalene, squalane, plastibase, and the like which are mixtures of various hydrocarbons.

Examples of higher alcohols usable as oleaginous bases include, for example, fatty series monohydric alcohols having 12 to 30 carbon atoms, such as lauryl alcohol, tridecyl alcohol, myristyl alcohol, pentadecyl alcohol, cetyl alcohol (cetanol), hexadecyl alcohol, heptadecyl alcohol, stearyl alcohol, oleyl alcohol, nonadecyl alcohol, eicosyl alcohol, ceryl alcohol, melissyl alcohol, and cetostearyl alcohol, and the like.

Examples of higher fatty acids usable as oleaginous bases include, for example, saturated or unsaturated fatty acids having 6 to 32 carbon atoms, such as caproic acid, enanthic acid, caprylic acid, pelargonic acid, capric acid, undecylic acid, lauric acid, tridecylic acid, myristic acid, pentadecylic acid, palmitic acid, heptadecylic acid, stearic acid, oleic acid, nonadecylic acid, arachic acid, arachidonic acid, linoleic acid, linolenic acid, behenic acid, lignoceric acid, cerotinic acid, heptacosanoic acid, montanoic acid, melissic acid, lacceric acid, elaidic acid, and brassidic acid, and the like.

Examples of higher fatty acid esters usable as oleaginous bases include, for example, fatty acid esters such as palmitic acid myristyl, stearic acid stearyl, myristic acid myristyl, lignoceric acid ceryl, cerotinic acid lacceryl, and lacceric acid lacceryl; esters of a fatty acid having 10 to 32 carbon atoms and a fatty series monohydric alcohol having 14 to 32 carbon atoms, encompassing animal-derived natural waxes such as lanolin, beeswax, spermaceti wax, and shellac wax and plant-derived natural waxes such as carnauba wax and candelilla wax; esters of a saturated or unsaturated fatty acid having 10 to 22 carbon atoms and a glycerin, such as glyceryl monolaurylate, glyceryl monomyristirate, glyceryl monooleate, glyceryl monostearate, glyceryl dilaurylate, glyceryl dimyristirate, glyceryl stearate, glyceryl trilaurylate, glyceryl trimyristirate, and glyceryl tristearate, or a hydrogenated product thereof; and the like.

Examples of glycols usable as oleaginous bases include, for example, ethylene glycol, diethylene glycol, propylene glycol, 1,3-butanediol, polyethylene glycol, and the like.

Examples of vegetable oils usable as oleaginous bases include, for example, camellia oil, castor oil, olive oil, cacao oil, coconut oil, palm oil, macadamia nut oil, soybean oil, tea seed oil, sesame oil, almond oil, safflower oil, cottonseed oil, turpentine oil, vegetable fats and oils in which these vegetable oils are hydrogenated, and the like.

Examples of animal oils usable as oleaginous bases include, for example, mink oil, egg yolk oil, squalane, squalene, lanolin, derivatives of animal oil, and the like.

Examples of emulsion bases include, for example, oil-in-water bases, water-in-oil bases, suspension bases, and the like. The emulsion bases may be used singly or in combination of two or more species thereof.

Examples of oil-in-water bases include bases in which ingredients, such as lanolin, propylene glycol, stearyl alcohol, vaseline, silicone oil, liquid paraffin, glyceryl monostearate, and polyethylene glycol, are emulsified and dispersed in an aqueous phase in the presence or absence of a surfactant; and the like. Oil-in-water bases can be used preferably in preparing cream and the like.

Examples of water-in-oil bases include bases in which ingredients, such as vaseline, higher aliphatic alcohol, and liquid paraffin, are emulsified and dispersed with the addition of water in the presence of a nonionic surfactant; and the like.

Oil-in-water bases and water-in-oil bases can preferably be used for dosage forms containing water, for example, liquid, lotion, cataplasm, ointment, and the like which each contain water.

Examples of suspension bases include aqueous bases in which suspending agents, such as starch, glycerin, high viscosity carboxymethyl cellulose, and carboxyvinyl polymer, are added to water and made gelatinous; and the like.

The pharmaceutical preparation according to the present invention can be manufactured by a generally adopted preparation method of external preparations. For example, ointments or creams can be manufactured by kneading, emulsifying, or suspending the raw materials of the bases in accordance with the respective dosage forms to thus prepare the bases, followed by adding effective ingredients and various additives and mixing them. For mixing, generally used mixing machines, such as a screw mixer, homomixer, kneader, and roll mill, can be used.

If the dosage form is lotion, it may be any of a suspension type, emulsion form, and solution type.

Examples of bases of a suspension type lotion include mixtures of water and a suspension of rubber such as gum arabic or gum traganth, cellulose such as methyl cellulose, hydroxyethyl cellulose, or hydroxyethyl starch, or clay such as bentonite or veegum HV; and the like. The bases of a suspension type lotion may usually be used singly or in mixture of two or more species thereof.

Examples of bases of an emulsion form lotion include bases in which water and an oily substance such as: fatty acid such as stearic acid, behenic acid, or oleic acid; or higher alcohol such as stearyl alcohol, cetanol, or behenyl alcohol are emulsified; and the like. The bases of an emulsion form lotion may usually be used singly or in mixture of two or more species thereof.

Examples of bases of a solution type lotion include alcohols such as water, ethanol, glycerin, and propylene glycol; and the like. The bases of a solution type lotion may usually be used singly or in mixture of two or more species thereof.

Lotions can be manufactured, for example, by adding various base ingredients to purified water and mixing them with stirring, followed by adding effective ingredients and additives and mixing them, and by filtration if desired.

For the dosage form of liniment, bases thereof include, for example, vegetable oils such as olive oil, sesame oil, almond oil, cottonseed oil, and turpentine oil, alcohols such as ethanol, propanol, and isopropanol, mixtures of them with water, and the like. The bases of a liniment may usually be used singly or in mixture of two or more species thereof.

Liniments can be manufactured by dissolving effective ingredients in a base, adding desired ingredients further, and mixing them.

For the dosage form of cataplasm, bases thereof include, for example, polyacryl acids and salts thereof; water-soluble high-molecular-weight compounds such as polyvinyl alcohol and polyvinyl pyrrolidone; crosslinked products such as bases in which the water-soluble high-molecular-weight compounds are crosslinked by a multivalent metal salt such as alum, and bases in which the water-soluble high-molecular-weight compounds are crosslinked by subjecting them to physical processing such as radiation irradiation; and the like. The bases of a cataplasm may usually be used singly or in mixture of two or more species thereof.

Cataplasms can be manufactured by mixing effective ingredients, bases, and desired additions, followed by heating and cooling them.

For the plaster, the patch, and the emplastrum, examples of ingredients include supports such as nonwoven fabric; elastic products such as natural rubber, styrene-butadiene rubber (SBR), butyl rubber, polyisobutylene, polyvinyl alkyl ether, polyurethane, dimethylpolysiloxane, styrene-isoprene-styrene rubber, and isoprene rubber; fillers such as zinc flower, titanium oxide, and silica; tackifiers, such as terpene resin, rosin or ester thereof, and phenol resin, which are compatible with elastic products; exfoliation treatment agents such as vinyl acetate, silicone resin, and polyvinyl chloride; softeners such as liquid paraffin and process oil; age resistors such as dibutylhydroxy toluene (BHT); and the like. These ingredients may be used singly or in mixture of two or more species thereof.

Plasters, patches, emplastrums, and the like can be manufactured by a conventional method such as a solution method or a heat and pressure method. Specifically, in the case of, for example, using a heat and pressure method, they can be manufactured in such a manner that effective ingredients and other ingredients are uniformly kneaded by a roll mill or the like, and applied on a released paper using a calender under heat and pressure in such a manner as to be uniformly thick, forming a drug-containing layer, which is layered and tightly adhered on the surface of a support, Also in the cases of gels, liquids, tapes, and the like, bases thereof are not limited to particular ones as long as they are used for usual external preparations.

First Medical Device

A first medical device according to the present invention is a medical device for preventing or treating rhinitis.

The first medical device according to the present invention includes a breathable mask portion covering the nostrils of a subject in need of prevention or treatment of rhinitis, an ear loop portion provided on the breathable mask portion, and composite particles detachably attached to the breathable mask portion, wherein the composite particle includes one or more titanium oxide particles, one or more metal particles, and one or more calcium phosphate particles.

Below, an embodiment of a first medical device according to the present invention will be described with reference to the drawings. FIG. 1 is a partially cutaway view illustrating one embodiment of a first medical device according to the present invention.

As illustrated in FIG. 1, the medical device 10 according to the present embodiment includes a breathable mask portion 11 covering the nostrils of a subject in need of prevention or treatment of rhinitis, ear loop portions 12a and 12b provided at the both ends of the breathable mask portion 11, and a composite particle 13 detachably attached to the breathable mask portion 11.

When the medical device 10 is put on a subject, the ear loop portion 12a is put around one ear of the subject, the ear loop portion 12b is put around the other ear of the subject, and at least the nostrils on the face of the subject are covered by the breathable mask portion 11. When the medical device 10 is put on a subject, the mouth of the subject in addition to the nostrils of the subject may be covered by the breathable mask portion 11.

As illustrated in FIG. 1, the form of the medical device 10 is the form of a flat type mask, but the form of the medical device 10 is not limited to the form of a flat type mask, and may be the form of a pleated type mask, a stereoscopic type mask, and the like, The breathable mask portion 11 is a mask body which covers the nostrils of a subject in need of prevention or treatment of rhinitis, and has breathability. The breathability of the breathable mask portion 11 can be adjusted, as appropriate, to the extent that a subject who wears the medical device 10 can breathe. The breathability of the breathable mask portion 11 is, for example, 5 to 150 $cm^3$/$cm^2$.sec, preferably 30 to 100 $cm^3/cm^2$.sec. Measurement of breathability is carried out in accordance with, for example, JIS L10968.27.1A Method (Frajour type method).

The breathable mask portion 11 is formed of a plurality of breathable sheet members which are superimposed. The edge portions of the plurality of breathable sheet members are joined by a known joining method such as heat welding, ultrasonic welding, and adhesive. The breathable mask portion 11 includes a first breathable sheet member 111, a second breathable sheet member 112, and a third breathable sheet member 113, which are superimposed in turn. When the medical device 10 is put on a subject, the first breathable sheet member 111 is disposed to the face side of the subject, and the third breathable sheet member 113 is disposed to the external air side. The number of breathable sheet members which constitute the breathable mask portion 11 can be changed, if appropriate. For example, one or two or more breathable sheet members may be provided between the first breathable sheet member 111 and the second breathable sheet member 112. In addition, one or two or more breathable sheet members may be provided between the second breathable sheet member 112 and the third breathable sheet member 113.

Each breathable sheet member can be formed of, for example, nonwoven fabric, woven fabric, knitting, and the like. Examples of fibers constituting each breathable sheet member include, for example, synthetic fiber, regenerated fiber, natural fiber, and the like. Examples of synthetic fibers include, for example, polyolefin-based fibers such as polyethylene and polypropylene, polyester-based fibers such as polyethylene terephthalate and polybutyrene terephthalate, polyamide-based fibers such as nylon, and the like. A synthetic fiber may be a composite fiber such as a core-clad type fiber. Examples of regenerated fibers include, for example, rayon, acetate, and the like. Examples of natural fibers include, for example, cotton and the like. Examples of nonwoven fabrics include, for example, spunbonded nonwoven fabric, thermobonded nonwoven fabric, spunlaced nonwoven fabric, air-through nonwoven fabric, meltblown nonwoven fabric, needle-punched nonwoven fabric, and the like. Examples of woven fabrics include, for example, gauze and the like. A nonwoven fabric may be a multilayer structure having two or more layers. Examples of such multilayer structures include, for example, SS structure (spunbonded-spunbonded 2-layer structure), SMS (spunbonded-meltblown-spunbonded 3-layer structure), and the like.

The mass per unit area of each breathable sheet member can be adjusted to the same degree as that of breathable sheet members used for commercially available household or medical masks. The mass per unit area of the first breathable sheet member 111 and the third breathable sheet member 113 can be adjusted, for example, in view of breathability. The mass per unit area of the second breathable sheet member 112 can be adjusted, for example, in view of filtering property. In a case in which one or two or more breathable sheet members are provided between the first breathable sheet member 111 and the second breathable sheet member 112, or in a case in which one or two or more breathable sheet members are provided between the second breathable sheet member 112 and the third breathable sheet member 113, the mass per unit area of these breathable sheet members can be adjusted in view of, for example, breathability or filtering property.

The ear loop portions 12a and 12b are formed of, for example, a string-like member. The string-like member preferably has stretchability. The string-like member is, for example, a stretchable string-like member made of rubber or plastic, or the like. The both ends of the ear loop portions 12a or 12b are fixed to the breathable mask portion 11 by, for example, a joining method such as sewing, whereby loops which can be put on the ears of a subject are formed.

The composite particle 13 includes one or more titanium oxide particles, one or more metal particles, and one or more calcium phosphate particles. To the composite particle, the aforementioned description applies.

The composite particles 13 stay attached to the breathable mask portion 11 in such a manner as to be detachable by the breathing of a subject wearing the medical device 10. Accordingly, when a subject wearing the medical device 10 breathes, part of the numerous composite particles 13 attached to the breathable mask portion 11*l* are detached and administered to the intranasal mucosa of the subject. In other words, utilizing the breathing of a subject wearing the medical device 10 enables the composite particles 13 to be administered to the intranasal mucosa of the subject, thereby enabling the prevention or treatment of rhinitis of the subject.

A subject to whom the medical device 10 is applied is usually a patient with rhinitis, preferably a patient with allergic rhinitis, but is not particularly limited thereto as long as the patient is in need of prevention or treatment of rhinitis.

The rhinitis to which the medical device 10 is applied is not limited to a particular symptom as long as it causes inflammation to the nasal mucosa and has a symptom such as sneezing, nasal discharge, or nasal congestion. Examples of rhinitides to which the medical device 10 is applied include, for example, infectious rhinitis, hypersensitive non-infectious rhinitis, stimulatory rhinitis, atrophic rhinitis, specific granulomatous rhinitis, and the like. The rhinitis to which the medical device 10 is applied is preferably infectious rhinitis, hypersensitive non-infectious rhinitis, or the like. The rhinitis to which the medical device 10 is applied is preferably hypersensitive non-infectious rhinitis, more preferably allergic rhinitis or nonallergic rhinitis, still more preferably allergic rhinitis. Allergic rhinitis may be perennial allergic rhinitis or seasonal allergic rhinitis. The medical device 10 can exert an excellent prevention or treatment effect on allergic rhinitides which have been considered difficult to prevent or treat, particularly perennial allergic rhinitis caused by house dust, mites, mold, and the like.

In this embodiment, the composite particles 13 are detachably attached to the second breathable sheet member 112 which is one of the plurality of sheet members constituting the breathable mask portion 11. The sheet member to which the composite particles 13 are detachably attached is not limited to the second breathable sheet member 112 but may be another breathable sheet member. The composite particles 13 may also be detachably attached to two or more breathable sheet members.

The total attached amount of composite particles per unit area of a breathable sheet member is not limited to a particular value, but the lower limit value of the total attached amount is usually 1 $g/m^2$, preferably 2 $g/m^2$, more preferably 3 $g/m^2$, still more preferably 4 $g/m^2$, still more preferably 5 $g/m^2$, and the upper limit value of the total attached amount is usually 20 $g/m^2$, preferably 15 $g/m^2$, more preferably 10 $g/m^2$.

The composite particles 13 can be detachably attached to a breathable sheet member via, for example, a binder resin. A breathable sheet member to which the composite particles 13 are detachably attached via a binder resin can be manufactured, for example, by supplying a breathable sheet member with a liquid mixture containing the composite particles 13 and a binder resin or immersing a breathable sheet member in a liquid mixture containing the composite particles 13 and a binder resin, followed by drying the breathable sheet member. A breathable sheet member to which the composite particles 13 are detachably attached via a binder resin can also be manufactured, for example, by supplying the raw fabric of a breathable sheet with a liquid mixture containing the composite particle 13 and a binder resin or immersing the raw fabric of a breathable sheet in a liquid mixture containing the composite particle 13 and a binder resin, followed by drying the raw fabric of the breathable sheet and then cutting a breathable sheet member out of the raw fabric of the breathable sheet.

The amount of binder resin contained in the liquid mixture is preferably 20 to 90 parts by mass, more preferably 30 to 85 parts by mass, still more preferably 40 to 80 parts by mass, relative to 100 parts by mass of composite particles. The amount of binder resin contained in the breathable sheet member is similar.

The total attached amount of composite particles and binder resin per unit area of a breathable sheet member is not limited to a particular value, but the lower limit value of the total attached amount is usually 2 $g/m^2$, preferably 3 $g/m^2$, more preferably 4 $g/m^2$, still more preferably 5 $g/m^2$, still more preferably 6 $g/m^2$, and the upper limit value of the total attached amount is usually 30 $g/m^2$, preferably 25 $g/m^2$, more preferably 20 $g/m^2$, still more preferably 15 $g/m^2$.

For the binder resin, known resins having adhesiveness may be used singly or in combination of two or more species thereof. Examples of binder resins include, for example: natural starch adhesives or natural resins, such as gelatin, gum arabic, shellac, dammar, elemi, and sandarac; semisynthetic starch adhesives or semisynthetic resins, such as methyl cellulose, ethyl cellulose, nitro cellulose, carboxymethyl cellulose, and acetate; polyester resin based on isophthalic acid, terephthalic acid, bisphenol, of vinyl ester; acrylic copolymer resins such as ethylene acrylic acid, ethylene acrylic acid ester, acryl ester vinyl, and methacrylic acid ester vinyl; urethane resins formed reaction of isocyanate derivative or isocyanurate derivative, such as tolylene dicysocyanate, 4,4'-diphenylmethanediisocyanate, or lysine ester triisocyanate, isocyanate derivative or isocyanurate derivative such as tolylene diisocyanate, and polyol such as polyester polyol, polyether polyol, acrylloylol, or phenolic polyol; halogenated polymers such as polyvinyl chloride and polyvinylidene chloride; acetal resins such as polyvinyl acetate, ethylene-vinyl acetate copolymer, polyvinyl chloride-vinyl acetate copolymer, polyacryl ester, polystyrene, and polyvinyl acetal; polycarbonate resins; cellulose resins such as cellulose acetate; polyolefin resins; synthetic starch adhesives or synthetic resins of amino resins and the like such as urea resin, melamine resin, and benzoguanamine resin; silicone resins including modified product, such as epoxy-modified, amino-modified, urethane-modified, alkyd-modified, or acryl-modified product, copolymer, and the like, encompassing silicone resins such as polyalkyl siloxane, polyalkyl hydrogen siloxane, polyalkylalkenyl siloxane, polyalkyl siliconate, polyalkalialkyl siliconate, and polyalkylphenyl siloxane; and fluorine resins such as polymer such as tetrafluoro ethylene or vinylidene fluoride, copolymer of monomer and another monomer, and the like. Among these, urethane resins and silicone resins are preferable, and urethane resins are particularly preferable, in view of adhesiveness and the like.

Inorganic binders instead of or in combination of binder resins may be used singly or in combination of two or more species thereof. Examples of inorganic binders include, for example: products obtained by decomposing hydrolysable silicon compounds such as alkyl silicate, halogenated silicon, and partial hydrolysate thereof; organic acid polysiloxane compounds and polycondensates thereof; phosphates such as silica, colloidal silica, water glass, silicon compound, and zinc phosphate; metal oxides such as zinc oxide and zirconium oxide; biphosphates; cements; gypsums; limes; frits for enamel; and the like.

A period of time during which the medical device 10 is worn is a time effective for prevention or treatment of rhinitis. The wearing time effective for prevention or treatment of rhinitis can be adjusted, if appropriate, depending on the amount of composite particles which are detachably attached to the breathable mask portion, the degree of rhinitis, the dosage regimen, and the like. The wearing time for the medical device 10 for each time is usually 30 to 120 minutes, preferably 30 to 90 minutes, more preferably 30 to 60 minutes. The frequency of wearing the medical device 10 per day is usually 1 to 10 times, preferably 2 to 8 times, more preferably 3 to 6 times, but is not particularly limited thereto. The wearing interval of the medical device 10 can be adjusted, if appropriate, taking into account the duration of the effect of prevention or treatment of rhinitis, and the like. In a case in which the medical device 10 has been put on the face of a subject in a period of one day on the basis of the aforementioned wearing time for each time and the aforementioned frequency of wearing per day, the expected duration of the effect of prevention or treatment of rhinitis is usually from a few hours to several days, although there are differences between individual subjects, and in a case in which the medical device 10 has been put on the face of a subject in a period of one to two weeks on the basis of the aforementioned wearing time for each time and the aforementioned frequency of wearing per day, the expected duration of the effect of prevention or treatment of rhinitis is usually from one week to two months, although there are differences between individual subjects.

Second Medical Device

A second medical device according to the present invention is a medical device for preventing or treating rhinitis, which is inserted for use into the nasal cavity of a subject in need of prevention or treatment of rhinitis.

The second medical device according to the present invention includes a sheet portion to be inserted into the nasal cavity of a subject and composite particles attached to the sheet portion, wherein the composite particle includes one or more titanium oxide particles, one or more metal particles, and one or more calcium phosphate particles.

Figure 2:
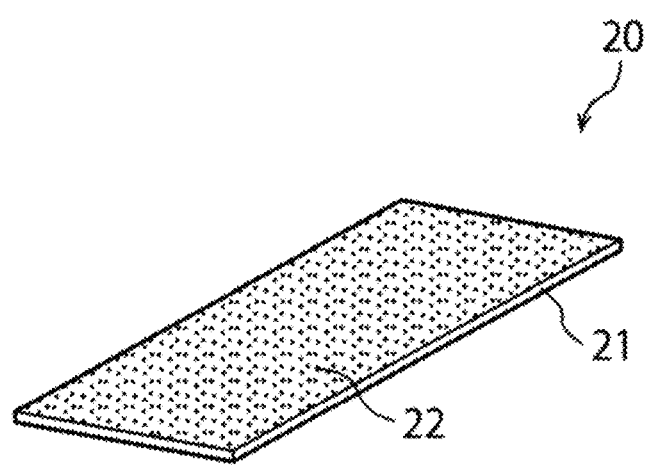
FIG. 2 is a perspective view illustrating one embodiment of a second medical device according to the present invention.

Below, an embodiment of the second medical device according to the present invention will be described with reference to the drawings. FIG. 2 is a perspective view illustrating one embodiment of the second medical device according to the present invention.

As illustrated in FIG. 2, the medical device 20 according to the embodiment includes a sheet portion 21 to be inserted into the nasal cavity of a subject and composite particles 22 attached to the sheet portion 21.

The medical device 20 is inserted for use into the nasal cavity of a subject in need of prevention or treatment of rhinitis. The medical device 20 may be deformed so that when the medical device 20 is inserted into the nasal cavity of a subject, the inserting can be easy. For example, the medical device 20 can be twisted into a shape of a twisted paper string and then inserted into the nasal cavity of a subject. As long as the part to which the composite particles 22 are attached of the sheet portion 21 is inserted into the nasal cavity of a subject, the whole of the medical device 20 may be inserted into the nasal cavity of a subject, or part of the medical device 20 may be inserted into the nasal cavity of a subject, and in view of ease of removal from the nasal cavity, part of the medical device 20 is preferably inserted into the nasal cavity of a subject with the remaining part hold outside of the nasal cavity of the subject. The medical device 20 is preferably inserted into the back in the nasal cavity (to the position having a distance of, for example 1 to 10 cm, preferably 1 to 8 cm, from the subnasal point). In addition, the medical device 20 is preferably inserted into the nasal cavity of a subject so that the part to which the composite particles 22 are attached of the sheet portion 21 can contact the intranasal mucosa of a subject.

The sheet portion 21 has a size which allows it to be inserted into the nasal cavity of a subject. The length of the sheet portion 21 is usually 50 to 300 mm, preferably 100 to 200 mm, and the width of the sheet portion 21 is usually 5 to 40 mm, preferably 10 to 20 mm. When the medical device 20 is inserted into the nasal cavity of a subject, for example, part of the sheet portion 21 (for example, a part 1 to 5 cm long) is hold outside of the nasal cavity without being inserted into the nasal cavity, and the remaining part of the sheet portion 21 is inserted into the nasal cavity of the subject. The sheet portion 21 is, for example, reed-shaped. The sheet portion 21 may have no breathability but preferably has breathability. The breathability of the sheet portion 21 can be adjusted, as appropriate, to the extent that a subject who has the inserted medical device 20 can breathe. The breathability of the sheet portion 21 is, for example, 5 to 150 $cm^3/cm^2.sec$, preferably 30 to 100 $cm^3/cm^2.sec$. Measurement of breathability is carried out in accordance with, for example, JIS L10968.27.1A Method (Frajour type method).

The sheet portion 21 can be formed of, for example, nonwoven fabric, woven fabric, knitting, plastic film having air holes, and the like. Examples of fibers constituting the sheet portion 21 include, for example, synthetic fiber, regenerated fiber, natural fiber, and the like. Examples of synthetic fibers include, for example, polyolefin-based fibers such as polyethylene and polypropylene, polyester-based fibers such as polyethylene terephthalate and polybutyrene terephthalate, polyamide-based fibers such as nylon, and the like. A synthetic fiber may be a composite fiber such as a core-clad type fiber. Examples of regenerated fibers include, for example, rayon, acetate, and the like. Examples of natural fibers include, for example, cotton and the like. Examples of nonwoven fabrics include, for example, spunbonded nonwoven fabric, thermobonded nonwoven fabric, spunlaced nonwoven fabric, air-through nonwoven fabric, nneltblown nonwoven fabric, needle-punched nonwoven fabric, and the like. Examples of woven fabrics include, for example, gauze and the like. A nonwoven fabric may be a multilayer structure having two or more layers. Examples of such multilayer structures include, for example, SS structure (spunbonded-spunbonded 2-layer structure), SMS (spunbonded-meltblown-spunbonded 3-layer structure), and the like.

The composite particle 22 includes one or more titanium oxide particles, one or more metal particles, and one or more calcium phosphate particles. To the composite particle, the aforementioned description applies.

The composite particles 22 may be attached to the sheet portion 21 in such a manner as to be detachable by the breathing of a subject into whose nasal cavity the medical device 20 is inserted, or may be attached to the sheet portion 21 so as not to be detached by the breathing of a subject into whose nasal cavity the medical device 20 is inserted.

When the medical device 20 is inserted into the nasal cavity of a subject, the composite particles 22 attached to the sheet portion 21 come into contact with or are attached to the intranasal mucosa of the subject. Accordingly, without utilizing the breathing of a subject, the composite particles 22 can be administered to the intranasal mucosa of the subject, thereby enabling the prevention or treatment of rhinitis of the subject.

A subject to whom the medical device 20 is applied is usually a patient with rhinitis, preferably a patient with allergic rhinitis, but is not particularly limited thereto as long as the patient is in need of prevention or treatment of rhinitis.

The rhinitis to which the medical device 20 is applied is not limited to a particular symptom as long as it has inflammation occurring to the nasal mucosa and has a symptom such as sneezing, nasal discharge, or nasal congestion. Examples of rhinitides to which the medical device 20 is applied include, for example, infectious rhinitis, hypersensitive non-infectious rhinitis, stimulatory rhinitis, atrophic rhinitis, specific granulomatous rhinitis, and the like. The rhinitis to which the medical device 20 is applied is preferably infectious rhinitis, hypersensitive non-infectious rhinitis, and the like. The rhinitis to which the medical device 20 is applied is preferably hypersensitive non-infectious rhinitis, more preferably allergic rhinitis or nonallergic rhinitis, still more preferably, allergic rhinitis. Allergic rhinitis may be perennial allergic rhinitis or seasonal allergic rhinitis. The medical device 20 can exert an excellent prevention or treatment effect on allergic rhinitides which have been considered difficult to prevent or treat, particularly perennial allergic rhinitis caused by house dust, mites, mold, and the like.

In a case in which the composite particles 22 are attached to the sheet portion 21 in such a manner as to be detachable by the breathing of a subject into whose nasal cavity the medical device 20 is inserted, part of the numerous composite particles 22 attached to the sheet portion 21 are detached and become attached to the intranasal mucosa of the subject as the subject into whose nasal cavity the medical device 20 is inserted breathes. Accordingly, utilizing the breathing of a subject into whose nasal cavity the medical device 20 is inserted enables the composite particles 22 to be administered to the intranasal mucosa of the subject, thereby enabling the prevention or treatment of rhinitis of the subject.

The total attached amount of composite particles per unit area of a sheet portion 21 is not limited to a particular value, but the lower limit value of the total attached amount is usually 1 $g/m^2$, preferably 2 $g/m^2$, more preferably 3 $g/m^2$, still more preferably 4 $g/m^2$, still more preferably 5 $g/m^2$, and the upper limit value of the total attached amount is usually 20 $g/m^2$, preferably 15 $g/m^2$, more preferably 10 $g/m^2$.

The composite particle 22 can be detachably attached to a sheet portion 21 via, for example, a binder resin. A sheet portion 21 to which the composite particle 22 is attached via a binder resin can be manufactured, for example, by drying the sheet member after supplying the sheet member with a liquid mixture containing the composite particle 22 and a binder resin or after immersing the sheet member in a liquid mixture containing the composite particle 22 and a binder resin. A sheet portion 21 to which the composite particle 22 is attached via a binder resin can also be manufactured, for example, by drying the raw fabric of the sheet and then cutting a sheet member out of the raw fabric of the sheet after supplying the raw fabric of the sheet with a liquid mixture containing the composite particle 22 and a binder resin or after immersing the raw material of the sheet in a liquid mixture containing the composite particle 22 and a binder resin.

The amount of binder resin contained in the liquid mixture is preferably 20 to 90 parts by mass, more preferably 30 to 85 parts by mass, still more preferably 40 to 80 parts by mass, relative to 100 parts by mass of composite particles. The amount of binder resin contained in the sheet portion 21 is similar.

The total attached amount of composite particles and binder resin per unit area of a sheet portion 21 is not limited to a particular value, but the lower limit value of the total attached amount is usually 2 $g/m^2$, preferably 3 $g/m^2$, more preferably 4 $g/m^2$, still more preferably 5 $g/m^2$, still more preferably 6 $g/m^2$, and the upper limit value of the total attached amount is usually 30 $g/m^2$, preferably 25 $g/m^2$, more preferably 20 $g/m^2$, still more preferably 15 $g/m^2$.

For the binder resin, known resins having adhesiveness may be used singly or in combination of two or more species thereof. Specific examples of binder resins are similar to the specific examples described with reference to the first medical device.

Inorganic binders instead of or in combination of binder resins may be used singly or in combination of two or more species thereof. Specific examples of inorganic binders are similar to the specific examples described with reference to the first medical device.

A period of time for which the medical device 20 stays inserted in the nasal cavity is a time effective for prevention or treatment of rhinitis. The inserted time effective for prevention or treatment of rhinitis can be adjusted if appropriate depending on the amount of the composite particles 22 which are attached to the sheet portion 21, the degree of rhinitis, the dosage regimen, and the like. The intranasal inserted time for the medical device 20 for each time is usually 10 to 60 minutes, preferably 20 to 60 minutes, more preferably 30 to 45 minutes. The frequency of inserting the medical device 20 intranasally per day is usually 1 to 3 times, preferably 1 to 2 times, more preferably 1 time, but is not particularly limited thereto. The interval of inserting the medical device 20 intranasally can be adjusted, taking into account the duration of the effect of prevention or treatment of rhinitis, and the like, if appropriate. In a case in which the medical device 20 has been inserted into the nasal cavity of a subject in a period of one day on the basis of the aforementioned inserted time for each time and the aforementioned frequency of inserting per day, the expected duration of the effect of prevention or treatment of rhinitis is usually from a few hours to several days, although there are differences between individual subjects, and in a case in which the medical device 20 has been inserted into the nasal cavity of a subject in a period of one to two weeks on the basis of the aforementioned inserted time for each time and the aforementioned frequency of inserting per day, the expected duration of the effect of prevention or treatment of rhinitis is usually from one week to two months, although there are differences between individual subjects.

Method

A method according to the present invention is a method for preventing or treating rhinitis.

The method according to the present invention includes the step of administering a composite particle to the intranasal mucosa of a subject in need of prevention or treatment of rhinitis, wherein the composite particle includes one or more titanium oxide particles, one or more metal particles, and one or more calcium phosphate particles. To the composite particle, the aforementioned description applies.

A subject to whom the method according to the present invention is applied is usually a patient with rhinitis, preferably a patient with allergic rhinitis, but is not particularly limited thereto as long as the subject is in need of prevention or treatment of rhinitis.

The rhinitis to which the method according to the present invention is applied is not limited to a particular symptom as long as it has inflammation occurring to nasal mucosa and has a symptom such as sneezing, nasal discharge, or nasal congestion. Examples of rhinitides to which the method according to the present invention is applied include, for example, infectious rhinitis, hypersensitive non-infectious rhinitis, stimulatory rhinitis, atrophic rhinitis, specific granulomatous rhinitis, and the like. The rhinitides to which the method according to the present invention are preferably infectious rhinitis, hypersensitive non-infectious rhinitis, and the like. The rhinitis to which the method according to the present invention is applied is preferably hypersensitive non-infectious rhinitis, more preferably allergic rhinitis or nonallergic rhinitis, still more preferably, allergic rhinitis. Allergic rhinitis may be perennial allergic rhinitis or seasonal allergic rhinitis. The method according to the present invention can exert an excellent prevention or treatment effect on allergic rhinitides which have been considered difficult to prevent or treat, particularly perennial allergic rhinitis caused by house dust, mites, mold, and the like.

A dose of composite particles is an amount effective for prevention or treatment of rhinitis. The amount effective for prevention or treatment of rhinitis can be adjusted, if appropriate, depending on the administration dosage form of the composite particles, the degree of rhinitis, the dosage regimen, and the like. A dose of composite particles for each time is usually 0.1 to 10 μg, preferably 0.2 to 5 μg, more preferably 0.4 to 4 μg. The frequency of administering the composite particles per day is usually 1 to 5 times, preferably 1 to 3 times, more preferably 1 to 2 times, but is not particularly limited thereto. The administration interval of the composite particles can be adjusted, if appropriate, taking into account the duration of the effect of prevention or treatment of rhinitis, and the like. In a case in which the composite particles have been administered to a subject in a period of one day on the basis of the aforementioned dose for each time and the aforementioned frequency of administration per day, the expected duration of the effect of prevention or treatment of rhinitis is usually from a few hours to several days, although there are differences between individual subjects, and in a case in which the composite particles have been administered to a subject in a period of one to two weeks on the basis of the aforementioned dose for each time and the aforementioned frequency of administration per day, the expected duration of the effect of prevention or treatment of rhinitis is usually from one week to two months, although there are differences between individual subjects.

In on embodiment of the method according to the present invention, the composite particles are administered to the intranasal mucosa of a subject in the administration step by administering the pharmaceutical preparation according to the present invention to the intranasal mucosa of the subject.

In on embodiment of the method according to the present invention, the composite particles are administered to the intranasal mucosa of a subject in the administration step by putting the first medical device according to the present invention on the face of the subject.

In on embodiment of the method according to the present invention, the composite particles are administered to the intranasal mucosa of a subject in the administration step by inserting the second medical device according to the present invention into the nasal cavity of the subject.

EXAMPLES

Below, the present invention will be described in further detail with reference to Manufacturing Examples and Test Examples. However, the scope of the present invention is not to be limited to these Manufacturing Examples and Test Examples.

Manufacturing Example 1

Manufacturing of Composite Particles

In this Manufacturing Example, titanium oxide powder, silver powder, and hydroxyapatite power were used as raw material powders, and composite particles including one or more titanium oxide particles, one or more silver particles, and one or more hydroxyapatite particles were manufactured.

In this Manufacturing Example, two composite particles M1 and M2 were manufactured. The composite particles M1 and M2 were different in the content ratio of titanium oxide, silver, and hydroxyapatite. The composite particles M1 and M2 were manufactured in the same manner as "Earth-plus™" manufactured and sold by Shinshu Ceramics Co., Ltd. (Nagano Prefecture, Japan). The manufacturing of the composite particles M1 and M2 was consigned to Shinshu Ceramics Co., Ltd.

The raw material powders shown in Table 1 were made ready for use. The particle size of the titanium oxide powder is the one which was measured using a transmission electron microscope (TEM) or a scanning electron microscope (SEM), the particle size of the silver powder is the one which was calculated on the basis of the specific surface area, and the particle size of the hydroxyapatite powder is the one which was measured by laser diffraction/scattering. The silver particles contained in the silver powder were inhibited from aggregating because the silver powder was kept refrigerated until it was used.

TABLE 1

| | Raw Material Powder | | |
|---|---|---|---|
| | Anatase Type Titanium Oxide Powder | Hydroxyapatite Powder | Silver Powder |
| CAS No. | 13463-67-7 | 10103-46-5 | 7440-22-4 |
| Purity | 95 wt % or more | 95 wt % or more | 95 wt % or more |
| Shape | powder | powder | powder |
| Color | white | white | — |
| Smell | none | none | none |
| Specific gravity | 3.9 | 2.7 | 10.5 |
| Particle size of primary particle | 0.03 to 0.1 μm | 0.1 to 0.2 μm | 1.1 to 1.9 μm |
| Particle size of secondary particle | 1 to 2 μm | 4 to 5 μm | — |
| pH | 6 to 8 | — | — |
| Melting point | 1823° C. or more | 1670° C. or more | 962° C. or more |

A commercially available wet bead mill ("STARMILL LME" from Ashizawa Finetech Ltd.) was used to mix titanium oxide powder, silver powder, hydroxyapatite powder, and a polycarboxylic acid dispersant in water, thereby compositing one or more titanium oxide particles included in the titanium oxide powder, one or more silver particles included in the silver powder, and one or more hydroxyapatite particles included in the hydroxyapatite powder, to manufacture a suspension (slurry) of composite particles. The wet bead mill used can pulverize titanium oxide particles, silver particles, and hydroxyapatite particles included in the raw material powder while dispersing them, whereby they can be made into fine particles as small as nanoparticles or submicron particles, and the fine particles can be composited, as well.

The conditions for compositing particles using the wet bead mill were as follows:
  the total addition amount of raw material powder: 4 kg or more
  cylinder volume: 3.3 L
  beads: beads made of zirconia (0.5 mm in diameter, 0.37 mg in mass)

flow rate of liquid: 2 L/minute
circumferential speed of blades in cylinder: 540 m/minute
liquid temperature: 35 to 45° C.
mixing time per kg of raw material powder: 30 to 40 minutes (about 36 minutes)

The total compounding amount of titanium oxide powder, silver powder, and hydroxyapatite powder was adjusted to 35 parts by mass relative to 65 parts by mass of water. The total compounding amount of polycarboxylic acid dispersant was adjusted to 0.5 parts by mass relative to 35 parts by mass of the total compounding amount of titanium oxide powder, silver powder, and hydroxyapatite powder.

In the manufacture of the composite particles M1, the compounding amount of titanium oxide powder was adjusted to about 160 parts by mass (155 to 165 parts by mass) relative to 1 part by mass of silver powder, and the compounding amount of hydroxyapatite powder was adjusted to about 40 parts by mass (39 to 41 parts by mass) relative to 1 part by mass of silver powder.

In the manufacture of the composite particles M2, the compounding amount of titanium oxide powder was adjusted to about 30 parts by mass (29 to 31 parts by mass) relative to 1 part by mass of silver powder, and the compounding amount of hydroxyapatite powder was adjusted to about 3 parts by mass (2.5 to 3.5 parts by mass) relative to 1 part by mass of silver powder.

The composite particles M1 and M2 were manufactured by drying a suspension (slurry) of composite particles. The particle size of composite particles M1 and M2, as measured by dynamic light scattering, was 200 to 500 nm. The median diameter (d50) of the composite particles M1 and M2, as measured by dynamic light scattering on a volumetric basis, was about 300 nm. The particle size by dynamic light scattering was measured using a commercially available dynamic light scattering type particle size distribution measuring device, specifically a dynamic light scattering type nano tracking particle size distribution measuring device, "UPA-EX150" (made by Nikkiso Co., Ltd.)

Manufacturing Example 2

Manufacturing of Composite-Particles-Attached Nonwoven Fabric

To the suspension (slurry) of the composite particles M1 obtained in Manufacturing Example 1, a binder resin was added to prepare a liquid mixture, whereafter a spunpond nonwoven fabric made of polyester was immersed in the liquid mixture, thereby impregnating the nonwoven fabric with the liquid mixture. After the immersing, the nonwoven fabric was removed from the liquid mixture and pressed with a roller to squeeze out the surplus liquid mixture. After the pressing, the nonwoven fabric was dried at about 130° C. for about one minute to manufacture a composite-particles-attached nonwoven fabric N1. As a binder resin, a urethane resin ($C_3H_7NO_2/NH_2COOC_2H_5$) was used.

By adjusting the concentrations of the composite particles M1 and the binder resin in the liquid mixture, the total attached amount (total fixed amount) of composite particles M1 and binder resin per unit area of the composite-particles-attached nonwoven fabric N1 was adjusted to 4 $g/m^2$, 6 $g/m^2$, 8 $g/m^2$, or 10 $g/m^2$.

The breakdown of 4 $g/m^2$ was 2.27 $g/m^2$ of titanium oxide, 0.571 $g/m^2$ of hydroxyapatite, 0.014 $g/m^2$ of silver, and 1.14 $g/m^2$ of binder resin.

The breakdown of 6 $g/m^2$ was 3.41 $g/m^2$ of titanium oxide, 0.857 $g/m^2$ of hydroxyapatite, 0.021 $g/m^2$ of silver, and 1.71 $g/m^2$ of binder resin.

The breakdown of 8 $g/m^2$ was 4.54 $g/m^2$ of titanium oxide, 1.143 $g/m^2$ of hydroxyapatite, 0.029 $g/m^2$ of silver, and 2.29 $g/m^2$ of binder resin.

The breakdown of 10 $g/m^2$ was 5.68 $g/m^2$ of titanium oxide, 1.428 $g/m^2$ of hydroxyapatite, 0.036 $g/m^2$ of silver, and 2.86 $g/m^2$ of binder resin.

A composite-particles-attached nonwoven fabric N2 was manufactured in the same manner as described above, except that a suspension of composite particles M2 was used in place of the suspension of the composite particles M1.

By adjusting the concentrations of the composite particles M2 and the binder resin in the liquid mixture, the total attached amount (total fixed amount) of composite particles M2 and binder resin per unit area of the composite-particles-attached nonwoven fabric N2 was adjusted to 13.5 $g/m^2$.

The breakdown of 13.5 $g/m^2$ was 6.525 $g/m^2$ of titanium oxide, 0.750 $g/m^2$ of hydroxyapatite, 0.225 $g/m^2$ of silver, and 6.00 $g/m^2$ of binder resin.

Figure 3:
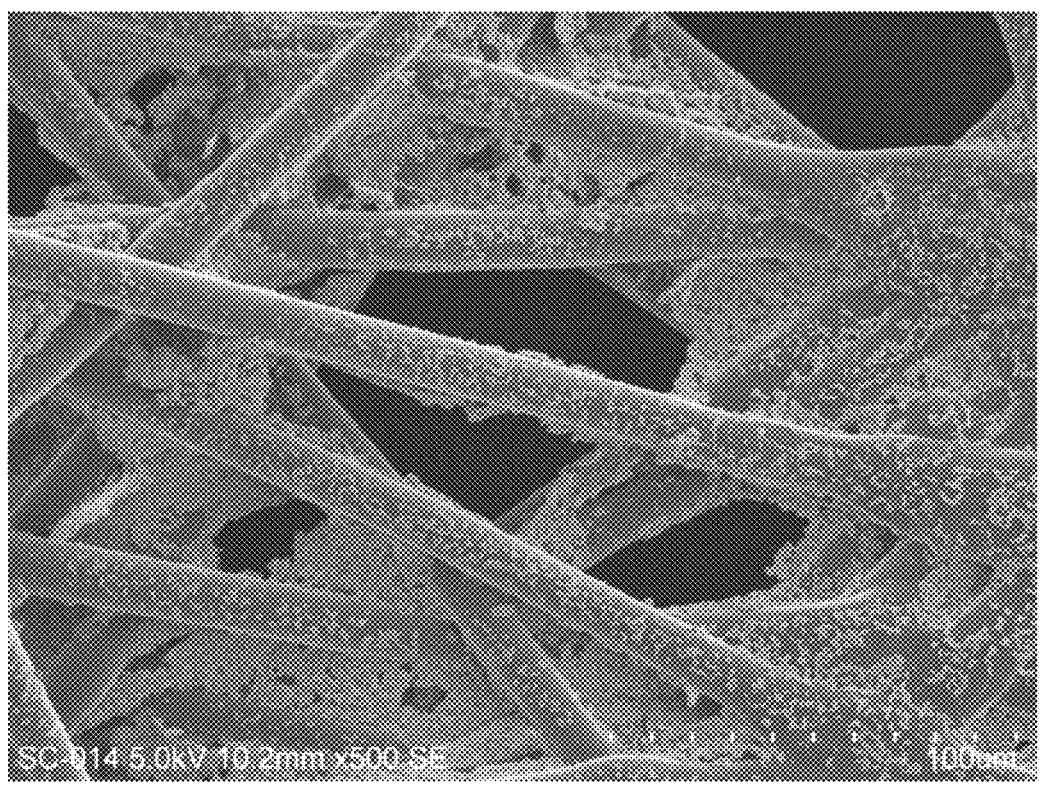
FIG. 3 is a view illustrating a result of the electron microscopic observation (500× magnification) of the composite-particles-attached nonwoven fabric manufactured in Manufacturing Example 2.
Figure 4:
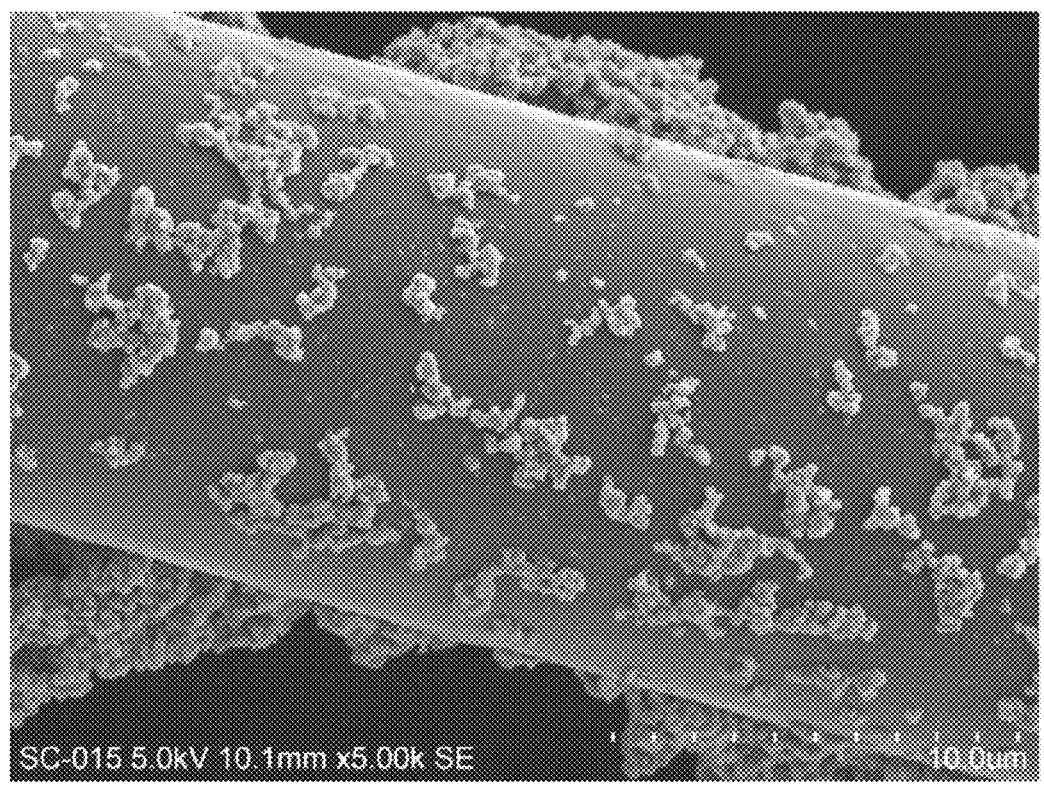
FIG. 4 is a view illustrating a result of the electron microscopic observation (5000× magnification) of the composite-particles-attached nonwoven fabric manufactured in Manufacturing Example 2.
Figure 5:
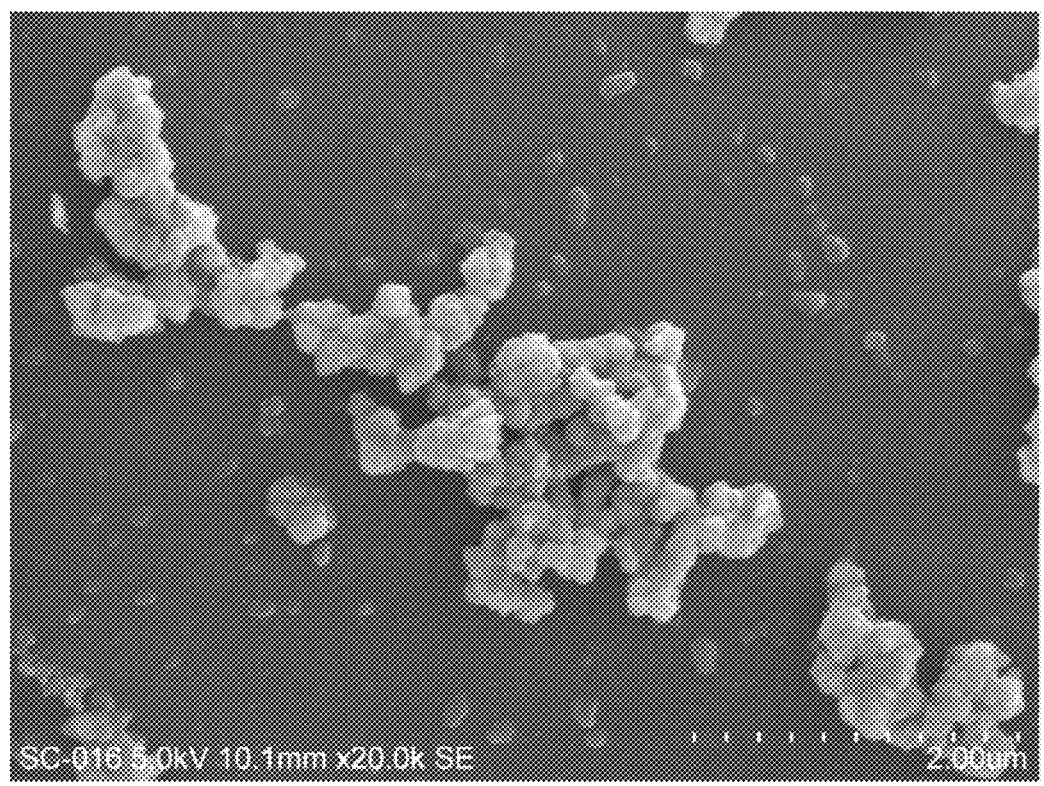
FIG. 5 is a view illustrating a result of the electron microscopic observation (20000× magnification) of the composite-particles-attached nonwoven fabric manufactured in Manufacturing Example 2.
Figure 6:
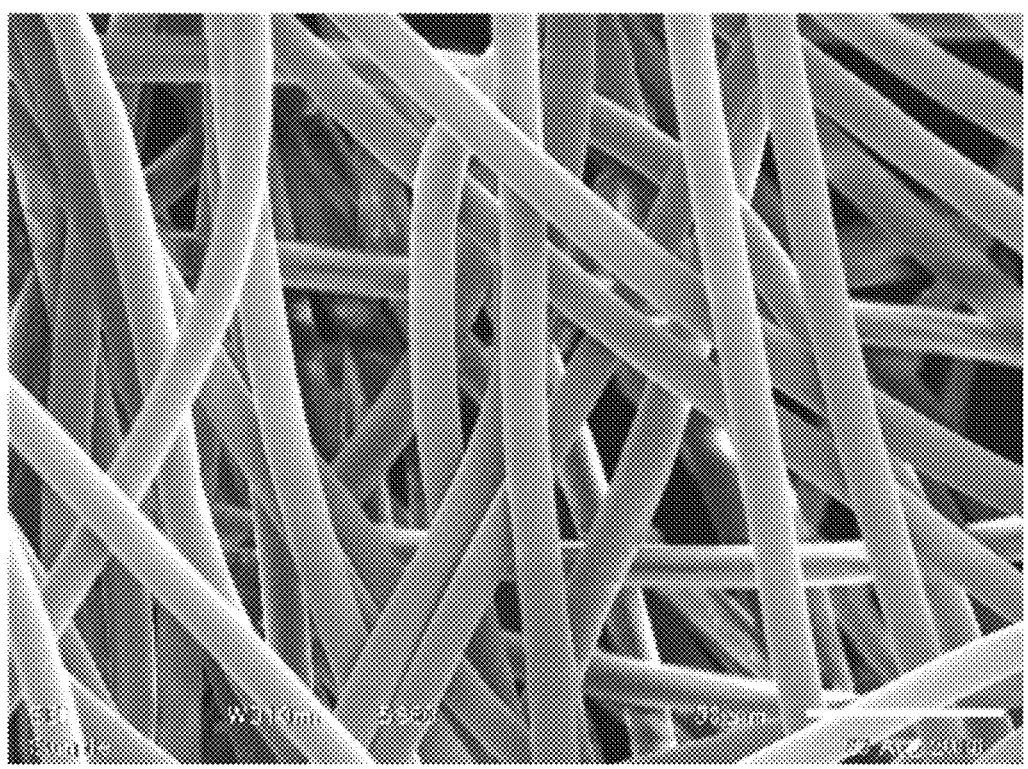
FIG. 6 is a view illustrating a result of the electron microscopic observation (500× magnification) of the nonwoven fabric with no composite particle attached.
Figure 7:
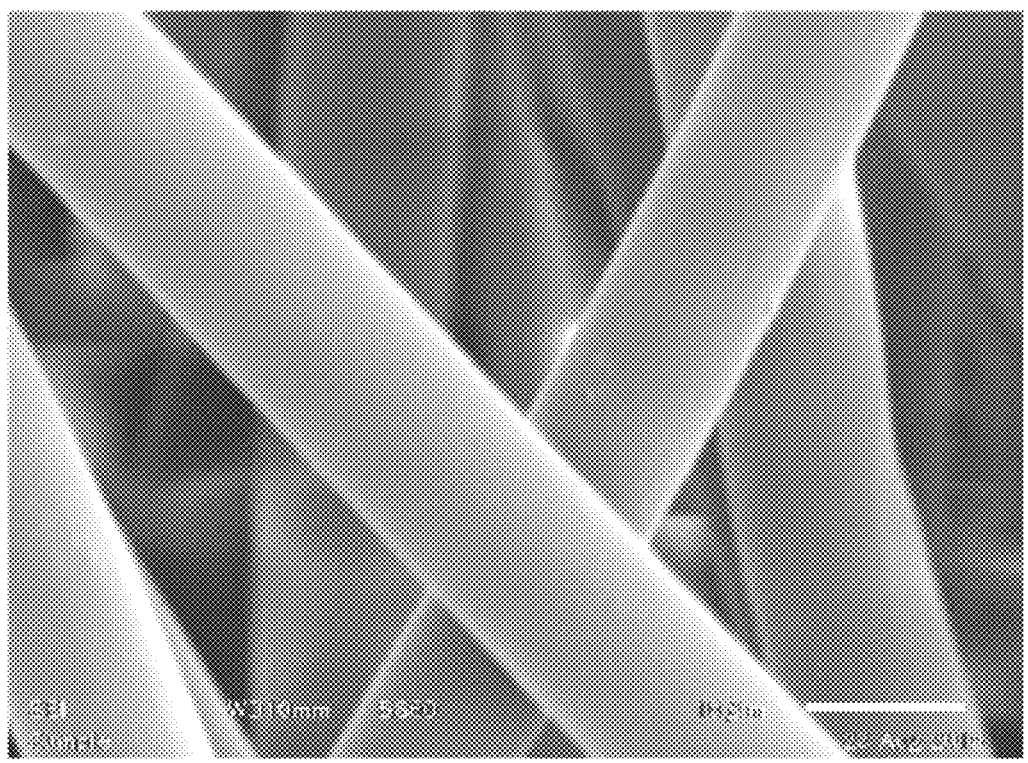
FIG. 7 is a view illustrating a result of the electron microscopic observation (1000× magnification) of the nonwoven fabric with no composite particle attached.

The composite-particles-attached nonwoven fabric N1 in which the total attached amount (total fixed amount) of composite particles M1 and binder resin was 4 $g/m^2$ was observed with an electron microscope. Results of the electron microscopic observation are shown in FIGS. 3 to 5. FIG. 3 shows an observation result at 500× magnification, FIG. 4 an observation result at 5000× magnification, and FIG. 5 an observation result at 20000× magnification. As shown in FIG. 3 to FIG. 5, the composite particles M1 attached to the nonwoven fabric were identified. In addition, electron microscopic observation results of the nonwoven fabric to which no composite particle was attached are shown as a control in FIG. 6 and FIG. 7. FIG. 6 shows an observation result at 500× magnification, and FIG. 7 an observation result at 1000× magnification.

Manufacturing Example 3

Manufacturing of Composite-Particles-Attached Sheet

The composite-particles-attached nonwoven fabric manufactured in Manufacturing Example 2 was cut to manufacture a reed-shaped composite-particles-attached sheet cm in width and 10 cm in length. As a composite-particles-attached nonwoven fabric, the composite-particles-attached nonwoven fabric N1 in which the total attached amount (total fixed amount) of composite particles M1 and binder resin was 4 $g/m^2$ was used.

Manufacturing Example 4

Manufacturing of Composite-Particles-Attached Mask

Composite-particles-attached masks were manufactured by layering a polypropylene spunbonded nonwoven fabric, a polypropylene meltblown nonwoven fabric, a composite-particles-attached nonwoven fabric, and a polypropylene spunbonded nonwoven fabric in this order from the external air side. As a composite-particles-attached nonwoven fabric, the composite-particles-attached nonwoven fabric N2 in which the total attached amount (total fixed amount) of composite particles M2 and binder resin was 13.5 $g/m^2$ was used.

Manufacturing Example 5

Manufacturing of Composite-Particles-Containing Ointment

Medical vaseline (white petrolatum according to the Japanese Pharmacopoeia, made by Kenei Pharmaceutical Co., Ltd.) and composite particles M1 were mixed to manufacture an ointment containing 1% by weight of composite particles M1.

Test Examples 1 to 6

In Test Examples 1 to 6, six patients (two males and four females) with perennial allergic rhinitis were designated as test subjects (see Table 2). All six test subjects experienced sneezing, nasal discharge, and nasal congestion, which are main symptoms of allergic rhinitis (hereinafter referred to as "three main symptoms"), substantially every time they do the cleaning and Japanese-futon-putting-down/away.

TABLE 2

| Test Subjects | | | | | | | |
|---|---|---|---|---|---|---|---|
| Test Subject No. | 1 | 2 | 3 | 4 | 5 | 6 | Average |
| Gender | male | female | female | male | female | female | |
| Age (years) | 47 | 26 | 26 | 48 | 39 | 25 | 35.17 |
| Age of allergic rhinitis onset (years) | 30 | 10 | 10 | 8 | 10 | 6 | 12.33 |
| Other allergic diseases | | AD | AD | | | AD | |
| Food allergy | No | No | Yes | No | No | No | |

AD: atopic dermatitis

The past history of each test subject is shown below.

[Test Subject No. 1]

It has been 17 years since he developed perennial allergic rhinitis. He has tried a lot of standard medical agents for allergic rhinitis so far, but none of them have given him satisfactory effects. The medical agents used were antihistaminic agents, antileukotriene agents, vasoconstrictors, intranasal steroid sprays, steroid oral medicines, various Chinese herbal medicines, and the like. These medical agents were weak in their effect and persistence, and alleviated the symptoms only a little.

[Test Subject No. 2]

It has been 16 years since she developed perennial allergic rhinitis. She has tried a lot of standard medical agents for allergic rhinitis so far, but none of them have given her satisfactory effects.

[Test Subject No. 3]

It has been 16 years since she developed perennial allergic rhinitis. She also suffers from asthma and food allergy.

[Test Subject No. 4]

It has been 40 years since she developed perennial allergic rhinitis. She has tried a lot of standard medical agents for allergic rhinitis so far, but none of them have given her satisfactory effects.

[Test Subject No. 5]

It has been 19 years since she developed perennial allergic rhinitis. She has tried a lot of standard medical agents for allergic rhinitis so far, but none of them have given her satisfactory effects.

[Test Subject No. 6]

It has been 19 years since she developed perennial allergic rhinitis. She has tried a lot of standard medical agents for allergic rhinitis so far, but none of them have given her satisfactory effects.

Test Example 1

Prevention Effect of Composite-Particles-Attached Mask on Allergic Rhinitis

In this Test Example, the composite-particles-attached mask manufactured in Manufacturing Example 4 was evaluated for prevention effect on allergic rhinitis.

The following tests were carried out for each test subject.

[Test A-1]

From 30 minutes before start of cleaning to start of cleaning: the test subjects each wore no mask.

From start of cleaning to finish of cleaning: the test subjects each started cleaning without wearing any mask, and finished cleaning 60 minutes after start of cleaning.

From finish of cleaning to 12 hours after finish of cleaning: the test subjects each wearing no mask were evaluated for the three main symptoms of allergic rhinitis.

[Test B-1]

From 30 minutes before start of cleaning to start of cleaning: the test subjects each wore a normal medical mask (surgical mask).

From start of cleaning to finish of cleaning: the test subjects each wearing a normal medical mask started cleaning, and finished cleaning 60 minutes after start of cleaning. They put off the masks when they finished cleaning.

From finish of cleaning to 12 hours after finish of cleaning: the test subjects each wearing no mask were evaluated for the three main symptoms of allergic rhinitis.

[Test C-1]

From 30 minutes before start of cleaning to start of cleaning: the test subjects each wore a composite-particles-attached mask.

From start of cleaning to finish of cleaning: the test subjects each wearing a composite-particles-attached mask started cleaning, and finished cleaning 60 minutes after start of cleaning. They put off the masks when they finished cleaning.

From finish of cleaning to 12 hours after finish of cleaning: the test subjects each wearing no mask were evaluated for the three main symptoms of allergic rhinitis.

The following items apply to each test.

When Test A-1, Test B-1, and Test C-1 were carried out to the same test subject, an interval of three days or more between Tests was allowed.

The start time of cleaning was 10 o'clock in the morning.

The cleaning items included the cleaning of an about eight-Japanese-tatami-mat bedroom using a vacuum cleaner, the putting-down/away of Japanese futon, the arrangement of books, and the wiping of a table top.

Evaluation of the three main symptoms was carried out with the following changes made to the evaluation criteria of the Practical Guideline for the Management of Allergic Rhinitis in Japan 2016 (the eighth revision) (written by the Committee of the Practical Guideline for the Management of Allergic Rhinitis in Japan, and published by Life Science Co., Ltd.)

The evaluation criteria in the Practical Guideline for the Management of Allergic Rhinitis in Japan are shown in Table 3.

The results of Test A-1, Test B-1, and Test C-1 are shown in Table 5.

TABLE 5

Results of Test A-1, Test B-1, and Test C-1

| Symptom | Test | \multicolumn{6}{c}{Patient No.} | Average Score |
| --- | --- | --- | --- | --- | --- | --- | --- | --- |
| | | 1 | 2 | 3 | 4 | 5 | 6 | |
| Paroxysmal sneeze | Test A-1 | 4 | 4 | 4 | 4 | 4 | 4 | 4.0 |
| | Test B-1 | 3 | 2 | 3 | 3 | 4 | 2 | 2.8 |
| | Test C-1 | 0 | 0 | 0 | 0 | 0 | 1 | 0.2 |
| Nasal discharge | Test A-1 | 4 | 4 | 4 | 4 | 4 | 4 | 4.0 |
| | Test B-1 | 3 | 3 | 3 | 3 | 4 | 3 | 3.2 |
| | Test C-1 | 1 | 0 | 0 | 0 | 0 | 2 | 0.5 |
| Nasal congestion | Test A-1 | 3 | 3 | 3 | 4 | 4 | 3 | 3.3 |
| | Test B-1 | 2 | 2 | 3 | 3 | 3 | 2 | 2.5 |
| | Test C-1 | 0 | 0 | 1 | 1 | 0 | 0 | 0.3 |

TABLE 3

Evaluation Criteria in the Practical Guideline for the Management of Allergic Rhinitis in Japan

| Symptom | Score | | | | |
| --- | --- | --- | --- | --- | --- |
| | 4 | 3 | 2 | 1 | 0 |
| Paroxysmal sneeze (average frequency of paroxysm per day) | 21 times or more | 20 to 11 times | 10 to 6 times | 5 to 1 times | score less than 1 |
| Nasal discharge (average frequency of nose blowing per day) | 21 times or more | 20 to 11 times | 10 to 6 times | 5 to 1 times | score less than 1 |
| Nasal congestion | completely congested all day | very heavily congested; mouth breathing for many hours per day | heavily congested; mouth breathing sometimes per day | no mouth breathing at all; some nose congestion | score less than 1 |

The evaluation criteria in the Practical Guideline for the Management of Allergic Rhinitis in Japan were used with the changes as shown in Table 4 because the three main symptoms in the 12 hours from finish of cleaning to 12 hours after finish of cleaning were evaluated in this Test.

In Test C-1 in which the composite-particles-attached masks were used, the occurrence of the three main symptoms of allergic rhinitis in each test subject was inhibited with a significant difference, compared to Test A-1 in which no masks were used and Test B-1 in which normal medical

TABLE 4

Evaluation Criteria in this Test

| Symptom | Score | | | | |
| --- | --- | --- | --- | --- | --- |
| | 4 | 3 | 2 | 1 | 0 |
| Paroxysmal sneeze (frequency of paroxysm in 12 hours) | 11 times or more | 10 to 6 times | 5 to 3 times | 2 to 1 times | score less than 1 |
| Nasal discharge (average frequency of nose blowing in 12 hours) | 11 times or more | 10 to 6 times | 5 to 3 times | 2 to 1 times | score less than 1 |
| Nasal congestion | completely congested for 12 hours | very heavily congested; mouth breathing for many hours in 12 hours | heavily congested; mouth breathing sometimes in 12 hours | no mouth breathing at all; some nose congestion | score less than 1 | masks were used. In addition, the effect of inhibiting the three main symptoms of allergic rhinitis from occurring was maintained for a few hours to several days after the composite-particles-attached masks were put off, although there were differences between individual test subjects.

This has revealed that the composite-particles-attached mask has the effect of preventing allergic rhinitis.

It is considered that the composite particles which are detached from the composite-particles-attached mask by the breathing of each test subject, inhaled into the nasal cavity, and attached to the intranasal mucosa inactivate (decompose) allergens (antigen proteins), such as house dust, mites, mold, and pollen, on the intranasal mucosa and inhibit antigen-antibody reactions on the intranasal mucosa, thereby exerting the prevention effect of the composite-particles-attached mask on allergic rhinitis.

Although there were differences between individual test subjects, however, the fact that the effect of inhibiting the three main symptoms of allergic rhinitis from occurring was maintained for a few hours to several days after the composite-particles-attached mask was put off suggests that the inactivation (decomposition) of allergens (antigen proteins) on the intranasal mucosa is not necessarily all involved in the prevention effect of the composite-particles-attached mask on allergic rhinitis.

There is considered to be a possibility that the composite particles attached to the intranasal mucosa modify allergen receptors on the intranasal mucosa, inhibiting antigen-antibody reactions on the intranasal mucosa, and that this is involved in the prevention effect of the composite-particles-attached mask on allergic rhinitis.

Test Example 2

Treatment Effect of Composite-Particles-Attached Mask on Allergic Rhinitis

In this Test Example, the composite-particles-attached mask manufactured in Manufacturing Example 4 was evaluated for treatment effect on allergic rhinitis. The following tests were carried out for each test subject.
[Test A-2]

From start of cleaning to occurrence of the three main symptoms: the test subjects each started cleaning without wearing any mask. The three main symptoms occurred to each test subject 10 to 30 minutes after start of cleaning.

From occurrence of the three main symptoms to finish of cleaning: the test subjects each continued to do the cleaning after occurrence of the three main symptoms, and finished cleaning 60 minutes after occurrence of the three main symptoms.

From finish of cleaning to 12 hours after finish of cleaning: the test subjects each wearing no mask were evaluated for the three main symptoms of allergic rhinitis.
[Test B-2]

From start of cleaning to occurrence of the three main symptoms: the test subjects each started cleaning without wearing any mask. The three main symptoms occurred to each test subject 10 to 30 minutes after start of cleaning.

From occurrence of the three main symptoms to finish of cleaning: the test subjects each continued to do the cleaning after occurrence of the three main symptoms, put a normal medical mask (surgical mask) on 10 minutes after occurrence of the three main symptoms, and finished cleaning 60 minutes after occurrence of the three main symptoms. They put off the masks when they finished cleaning.

From finish of cleaning to 12 hours after finish of cleaning: the test subjects each wearing no mask were evaluated for the three main symptoms of allergic rhinitis.
[Test C-2]

From start of cleaning to occurrence of the three main symptoms: the test subjects each started cleaning without wearing any mask. The three main symptoms occurred to each test subject 10 to 30 minutes after start of cleaning.

From occurrence of the three main symptoms to finish of cleaning: the test subjects each continued to do the cleaning after occurrence of the three main symptoms, put the composite-particles-attached mask on 10 minutes after occurrence of the three main symptoms, and finished cleaning 60 minutes after occurrence of the three main symptoms. They put off the masks when they finished cleaning.

From finish of cleaning to 12 hours after finish of cleaning: the test subjects each wearing no mask were evaluated for the three main symptoms of allergic rhinitis.

The following items apply to each test.

When Test A-2, Test B-2, and Test C-2 were carried out to the same test subject, an interval of three days or more between Tests was allowed.

The start time of cleaning was 10 o'clock in the morning.

The cleaning items included the cleaning of an about eight-Japanese-tatami-mat bedroom using a vacuum cleaner, the putting-down/away of Japanese futon, the arrangement of books, and the wiping of a table top.

Evaluation of the three main symptoms was carried out with the aforementioned changes made to the evaluation criteria of the Practical Guideline for the Management of Allergic Rhinitis in Japan 2016 (the eighth revision) (written by the Committee of the Practical Guideline for the Management of Allergic Rhinitis in Japan, and published by Life Science Co., Ltd.)

The results of Test A-2, Test B-2, and Test C-2 are shown in Table 6.

TABLE 6

Results of Test A-2, Test B-2, and Test C-2

| Symptom | Test | Patient No. | | | | | | Average Score |
|---|---|---|---|---|---|---|---|---|
| | | 1 | 2 | 3 | 4 | 5 | 6 | |
| Paroxysmal sneeze | Test A-2 | 3 | 4 | 4 | 4 | 3 | 3 | 3.5 |
| | Test B-2 | 3 | 4 | 4 | 4 | 3 | 3 | 3.5 |
| | Test C-2 | 0 | 0 | 0 | 0 | 1 | 0 | 0.2 |
| Nasal discharge | Test A-2 | 3 | 4 | 4 | 4 | 3 | 4 | 3.7 |
| | Test B-2 | 3 | 4 | 4 | 4 | 3 | 4 | 3.7 |
| | Test C-2 | 1 | 0 | 0 | 0 | 1 | 1 | 0.5 |
| Nasal congestion | Test A-2 | 3 | 3 | 3 | 4 | 3 | 4 | 3.3 |
| | Test B-2 | 3 | 3 | 3 | 4 | 3 | 4 | 3.3 |
| | Test C-2 | 1 | 0 | 1 | 0 | 1 | 1 | 0.7 |

In Test C-2 in which the composite-particles-attached masks were used, the persistence of the three main symptoms of allergic rhinitis in each test subject was inhibited with a significant difference, compared to Test A-2 in which no masks were used and Test B-2 in which normal medical masks were used. In addition, the effect of inhibiting the three main symptoms of allergic rhinitis from occurring was maintained for a few hours to several days after the composite-particles-attached masks were put off, although there were differences between individual test subjects.

This has revealed that the composite-particles-attached mask has the effect of treating allergic rhinitis.

It is considered that the composite particles which are detached from the composite-particles-attached mask by the breathing of each test subject, inhaled into the nasal cavity, and attached to the intranasal mucosa inactivate (decompose) allergens (antigen proteins), such as house dust, mites, mold, and pollen, on the intranasal mucosa and inhibit antigen-antibody reactions on the intranasal mucosa, thereby exerting the treatment effect of the composite-particles-attached mask on allergic rhinitis.

Although there were differences between individual test subjects, however, the fact that the effect of inhibiting the three main symptoms of allergic rhinitis from occurring was maintained for a few hours to several days after the composite-particles-attached mask was put off suggests that the inactivation (decomposition) of allergens (antigen proteins) on the intranasal mucosa is not necessarily all involved in the treatment effect of the composite-particles-attached mask on allergic rhinitis.

There is considered to be a possibility that the composite particles attached to the intranasal mucosa modify allergen receptors on the intranasal mucosa, inhibiting antigen-antibody reactions on the intranasal mucosa, and that this is involved in the treatment effect of the composite-particles-attached mask on allergic rhinitis.

Test Example 3

Prevention Effect of Composite-Particles-Containing Ointment on Allergic Rhinitis In this Test Example, the composite-particles-containing ointment manufactured in Manufacturing Example 5 was evaluated for prevention effect on allergic rhinitis.

The following tests were carried out for each test subject.
[Test A-3]

From 30 minutes before start of cleaning to start of cleaning: no ointments were applied to the intranasal mucosa of each test subject.

From start of cleaning to finish of cleaning: the test subjects each started cleaning, and finished cleaning 30 minutes after start of cleaning.

From finish of cleaning to 12 hours after finish of cleaning: the test subjects each were evaluated for the three main symptoms of allergic rhinitis.
[Test B-3]

30 minutes before start of cleaning to start of cleaning: 30 minutes before start of cleaning, 0.1 g of the same medical vaseline (not containing composite particles) as was used to manufacture composite-particle-containing ointment was applied to the intranasal mucosa (about 5 cm from the subnasal point) of each test subject with a swab.

From start of cleaning to finish of cleaning: the test subjects each started cleaning, and finished cleaning 30 minutes after start of cleaning.

From finish of cleaning to 12 hours after finish of cleaning: the test subjects each were evaluated for the three main symptoms of allergic rhinitis.
[Test C-3]

30 minutes before start of cleaning to start of cleaning: 30 minutes before start of cleaning, 0.1 g of composite-particle-containing ointment was applied to the intranasal mucosa (about 5 cm from the subnasal point) of each test subject with a swab.

From start of cleaning to finish of cleaning: the test subjects each started cleaning, and finished cleaning 30 minutes after start of cleaning.

From finish of cleaning to 12 hours after finish of cleaning: the test subjects each were evaluated for the three main symptoms of allergic rhinitis.

The following items apply to each test.

When Test A-3, Test B-3, and Test C-3 were carried out to the same test subject, an interval of three days or more between Tests was allowed.

The start time of cleaning was 10 o'clock in the morning.

The cleaning items included the cleaning of an about eight-Japanese-tatami-mat bedroom using a vacuum cleaner, the putting-down/away of Japanese futon, the arrangement of books, and the wiping of a table top.

Evaluation of the three main symptoms was carried out with the aforementioned changes made to the evaluation criteria of the Practical Guideline for the Management of Allergic Rhinitis in Japan 2016 (the eighth revision) (written by the Committee of the Practical Guideline for the Management of Allergic Rhinitis in Japan, and published by Life Science Co., Ltd.)

The results of Test A-3, Test B-3, and Test C-3 are shown in Table 7.

TABLE 7

Results of Test A-3, Test B-3, and Test C-3

| Symptom | Test | Patient No. 1 | 2 | 3 | 4 | 5 | 6 | Average Score |
|---|---|---|---|---|---|---|---|---|
| Paroxysmal sneeze | Test A-3 | 3 | 2 | 4 | 4 | 4 | 3 | 3.3 |
| | Test B-3 | 3 | 2 | 3 | 4 | 4 | 3 | 3.2 |
| | Test C-3 | 0 | 1 | 0 | 0 | 0 | 1 | 0.3 |
| Nasal discharge | Test A-3 | 4 | 4 | 4 | 4 | 4 | 4 | 4.0 |
| | Test B-3 | 3 | 4 | 3 | 4 | 3 | 4 | 3.5 |
| | Test C-3 | 0 | 1 | 0 | 0 | 1 | 2 | 0.7 |
| Nasal congestion | Test A-3 | 3 | 3 | 3 | 4 | 4 | 4 | 3.5 |
| | Test B-3 | 4 | 3 | 4 | 4 | 4 | 3 | 3.7 |
| | Test C-3 | 1 | 1 | 2 | 1 | 0 | 0 | 0.8 |

In Test C-3 in which the composite-particles-containing ointment was used, the occurrence of the three main symptoms of allergic rhinitis in each test subject was inhibited with a significant difference, compared to Test A-3 in which no ointment was used and Test B-3 in which normal medical vaseline was used. In addition, the effect of inhibiting the three main symptoms of allergic rhinitis from occurring was maintained for a few hours to several days after the composite-particles-containing powder was applied, although there were differences between individual test subjects.

This has revealed that the composite-particles-containing ointment has the effect of preventing allergic rhinitis.

It is considered that the composite particles in the composite-particles-containing ointment applied to the intranasal mucosa inactivate (decompose) allergens (antigen proteins), such as house dust, mites, mold, and pollen, on the intranasal mucosa and inhibit antigen-antibody reactions on the intranasal mucosa, thereby exerting the prevention effect of the composite-particles-containing ointment on allergic rhinitis.

Although there were differences between individual test subjects, however, the fact that the effect of inhibiting the three main symptoms of allergic rhinitis from occurring was maintained for a few hours to several days after the composite-particles-containing ointment was applied suggests that the inactivation (decomposition) of allergens (antigen proteins) on the intranasal mucosa is not necessarily all involved in the prevention effect of the composite-particles-containing ointment on allergic rhinitis.

There is considered to be, for example, a possibility that the composite particles attached to the intranasal mucosa modify allergen receptors on the intranasal mucosa, inhibiting antigen-antibody reactions on the intranasal mucosa, and that this is involved in the prevention effect of the composite-particles-containing ointment on allergic rhinitis.

Test Example 4

Treatment Effect of Composite-Particles-Containing Ointment on Allergic Rhinitis In this Test Example, the composite-particles-containing ointment manufactured in Manufacturing Example 5 was evaluated for treatment effect on allergic rhinitis. The following tests were carried out for each test subject.

[Test A-4]

From start of cleaning to occurrence of the three main symptoms: the test subjects each started cleaning with no ointments applied to the intranasal mucosa of each test subject. The three main symptoms occurred to each test subject 10 to 30 minutes after start of cleaning.

From occurrence of the three main symptoms to finish of cleaning: the test subjects each continued to do the cleaning after occurrence of the three main symptoms, and finished cleaning 40 minutes after occurrence of the three main symptoms.

From finish of cleaning to 12 hours after finish of cleaning: the test subjects each were evaluated for the three main symptoms of allergic rhinitis.

[Test B-4]

From start of cleaning to occurrence of the three main symptoms: the test subjects each started cleaning with no ointments applied to the intranasal mucosa of each test subject. The three main symptoms occurred to each test subject 10 to 30 minutes after start of cleaning.

From occurrence of the three main symptoms to finish of cleaning: the test subjects each continued to do the cleaning after occurrence of the three main symptoms, applied 0.1 g of the same medical vaseline (not containing composite particles) as was used to manufacture composite-particle-containing ointment to the intranasal mucosa (about 5 cm from the subnasal point) with a swab 10 minutes after occurrence of the three main symptoms, and finished cleaning 40 minutes after occurrence of the three main symptoms.

From finish of cleaning to 12 hours after finish of cleaning: the test subjects each were evaluated for the three main symptoms of allergic rhinitis.

[Test C-4]

From start of cleaning to occurrence of the three main symptoms: the test subjects each started cleaning with no ointments applied to the intranasal mucosa of each test subject. The three main symptoms occurred to each test subject 10 to 30 minutes after start of cleaning.

From occurrence of the three main symptoms to finish of cleaning: the test subjects each applied 0.1 g of composite-particle-containing ointment to the intranasal mucosa (about 5 cm from the subnasal point) with a swab 10 minutes after occurrence of the three main symptoms, and finished cleaning 40 minutes after occurrence of the three main symptoms.

From finish of cleaning to 12 hours after finish of cleaning: the test subjects each were evaluated for the three main symptoms of allergic rhinitis.

The following items apply to each test.

When Test A-4, Test B-4, and Test C-4 were carried out to the same test subject, an interval of three days or more between Tests was allowed.

The start time of cleaning was 10 o'clock in the morning.

The cleaning items included the cleaning of an about eight-Japanese-tatami-mat bedroom using a vacuum cleaner, the putting-down/away of Japanese futon, the arrangement of books, and the wiping of a table top.

Evaluation of the three main symptoms was carried out with the aforementioned changes made to the evaluation criteria of the Practical Guideline for the Management of Allergic Rhinitis in Japan 2016 (the eighth revision) (written by the Committee of the Practical Guideline for the Management of Allergic Rhinitis in Japan, and published by Life Science Co., Ltd.)

The results of Test A-4, Test B-4, and Test C-4 are shown in Table 8.

TABLE 8

Results of Test A-4, Test B-4, and Test C-4

| Symptom | Test | Patient No. | | | | | | Average Score |
|---|---|---|---|---|---|---|---|---|
| | | 1 | 2 | 3 | 4 | 5 | 6 | |
| Paroxysmal sneeze | Test A-4 | 3 | 4 | 4 | 4 | 3 | 4 | 3.7 |
| | Test B-4 | 3 | 4 | 4 | 4 | 3 | 3 | 3.5 |
| | Test C-4 | 0 | 0 | 0 | 0 | 1 | 1 | 0.3 |
| Nasal discharge | Test A-4 | 3 | 4 | 4 | 4 | 3 | 4 | 3.7 |
| | Test B-4 | 3 | 4 | 4 | 4 | 3 | 4 | 3.7 |
| | Test C-4 | 1 | 0 | 0 | 0 | 1 | 1 | 0.5 |
| Nasal congestion | Test A-4 | 4 | 3 | 3 | 4 | 3 | 4 | 3.5 |
| | Test B-4 | 3 | 3 | 3 | 4 | 3 | 4 | 3.3 |
| | Test C-4 | 2 | 0 | 1 | 1 | 1 | 1 | 1.0 |

In Test C-4 in which the composite-particles-containing ointment was used, the persistence of the three main symptoms of allergic rhinitis in each test subject was inhibited with a significant difference, compared to Test A-4 in which no ointment was used and Test B-4 in which normal medical vaseline was used. In addition, the effect of inhibiting the three main symptoms of allergic rhinitis from occurring was maintained for a few hours to several days after the composite-particles-containing ointment was applied, although there were differences between individual test subjects.

This has revealed that the composite-particles-containing ointment has the effect of treatment allergic rhinitis.

It is considered that the composite particles in the composite-particles-containing ointment applied to the intranasal mucosa inactivate (decompose) allergens (antigen proteins), such as house dust, mites, mold, and pollen, on the intranasal mucosa and inhibit antigen-antibody reactions on the intranasal mucosa, thereby exerting the treatment effect of the composite-particles-containing ointment on allergic rhinitis.

Although there were differences between individual test subjects, however, the fact that the effect of inhibiting the three main symptoms of allergic rhinitis from occurring was maintained for a few hours to several days after the composite-particles-containing ointment was applied suggests that the inactivation (decomposition) of allergens (antigen proteins) on the intranasal mucosa is not necessarily all involved in the treatment effect of the composite-particles-containing ointment on allergic rhinitis.

There is considered to be a possibility that the composite particles attached to the intranasal mucosa modify allergen receptors on the intranasal mucosa, inhibiting antigen-antibody reactions on the intranasal mucosa and that this is involved in the treatment effect of the composite-particles-containing ointment on allergic rhinitis.

Test Example 5

Prevention Effect of Composite-Particles-Attached Sheet on Allergic Rhinitis

In this Test Example, the composite-particles-attached sheet manufactured in Manufacturing Example 3 was evaluated for prevention effect on allergic rhinitis. The following tests were carried out for each test subject.

[Test A-5]

From 30 minutes before start of cleaning to start of cleaning: nothing was inserted to the nasal cavity of each test subject.

From start of cleaning to finish of cleaning: the test subjects each started cleaning, and finished cleaning 30 minutes after start of cleaning.

From finish of cleaning to 12 hours after finish of cleaning: the test subjects each with nothing inserted into their nasal cavity were evaluated for the three main symptoms of allergic rhinitis.

[Test B-5]

30 minutes before start of cleaning to start of cleaning: 30 minutes before start of cleaning, the test subjects each inserted the same nonwoven fabric (not containing composite particles) as was used to manufacture composite-particles-attached sheets into the back in the nasal cavity (inferior nasal concha) (about 1 to 8 cm from the subnasal point).

From start of cleaning to finish of cleaning: the test subjects each started cleaning, and finished cleaning 30 minutes after start of cleaning. They put off the nonwoven fabrics when they finished cleaning.

From finish of cleaning to 12 hours after finish of cleaning: the test subjects each with nothing inserted into their nasal cavity were evaluated for the three main symptoms of allergic rhinitis.

[Test C-5]

30 minutes before start of cleaning to start of cleaning: 30 minutes before start of cleaning, the test subjects each inserted a composite-particles-attached sheet into the back in the nasal cavity (inferior nasal concha) (about 1 to 8 cm from the subnasal point).

From start of cleaning to finish of cleaning: the test subjects each started cleaning, and finished cleaning 30 minutes after start of cleaning. They put off the composite-particles-attached sheets when they finished cleaning.

From finish of cleaning to 12 hours after finish of cleaning: the test subjects each with nothing inserted into their nasal cavity were evaluated for the three main symptoms of allergic rhinitis.

The following items apply to each test.

When Test A-5, Test B-5, and Test C-5 were carried out to the same test subject, an interval of three days or more between Tests was allowed.

The start time of cleaning was 10 o'clock in the morning.

The cleaning items included the cleaning of an about eight-Japanese-tatami-mat bedroom using a vacuum cleaner, the putting-down/away of Japanese futon, the arrangement of books, and the wiping of a table top.

Evaluation of the three main symptoms was carried out with the aforementioned changes made to the evaluation criteria of the Practical Guideline for the Management of Allergic Rhinitis in Japan 2016 (the eighth revision) (written by the Committee of the Practical Guideline for the Management of Allergic Rhinitis in Japan, and published by Life Science Co., Ltd.)

The results of Test A-5, Test B-5, and Test C-5 are shown in Table 9.

TABLE 9

Results of Test A-5, Test B-5, and Test C-5

| Symptom | Test | 1 | 2 | 3 | 4 | 5 | 6 | Average Score |
|---|---|---|---|---|---|---|---|---|
| Paroxysmal sneeze | Test A-5 | 3 | 3 | 4 | 4 | 3 | 4 | 3.5 |
| | Test B-5 | 4 | 4 | 4 | 4 | 3 | 4 | 3.8 |
| | Test C-5 | 0 | 0 | 0 | 0 | 0 | 1 | 0.2 |
| Nasal discharge | Test A-5 | 3 | 4 | 4 | 4 | 3 | 4 | 3.7 |
| | Test B-5 | 4 | 4 | 3 | 4 | 3 | 4 | 3.7 |
| | Test C-5 | 1 | 0 | 0 | 0 | 1 | 0 | 0.3 |
| Nasal congestion | Test A-5 | 3 | 4 | 3 | 4 | 3 | 3 | 3.3 |
| | Test B-5 | 3 | 4 | 3 | 4 | 4 | 4 | 3.7 |
| | Test C-5 | 0 | 0 | 1 | 1 | 0 | 0 | 0.3 |

In Test C-5 in which the composite-particles-attached sheets were used, the occurrence of the three main symptoms of allergic rhinitis in each test subject was inhibited with a significant difference, compared to Test A-5 in which no sheets were used and Test B-5 in which normal nonwoven fabrics (not containing composite particles) were used. In addition, the effect of inhibiting the three main symptoms of allergic rhinitis from occurring was maintained for a few hours to several days after the composite-particles-attached sheets were put off, although there were differences between individual test subjects.

This has revealed that the composite-particles-attached sheet has the effect of preventing allergic rhinitis.

It is considered that either or both the composite particles present on the parts of the composite-particles-attached sheet which are in contact with the intranasal mucosa or/and the composite particles which are detached from the composite-particles-attached sheet by the breathing of each test subject and attached to the intranasal mucosa inactivate (decompose) allergens (antigen proteins), such as house dust, mites, mold, and pollen, on the intranasal mucosa and inhibit antigen-antibody reactions on the intranasal mucosa, thereby exerting the prevention effect of the composite-particles-attached sheet on allergic rhinitis.

Although there were differences between individual test subjects, the fact that the effect of inhibiting the three main symptoms of allergic rhinitis from occurring was maintained for a few hours to several days after the composite-particles-attached sheet was put off suggests that the inactivation (decomposition) of allergens (antigen proteins) on the intranasal mucosa is not necessarily all involved in the prevention effect of the composite-particles-attached sheet on allergic rhinitis.

There is considered to be a possibility that the composite particles which have been put into contact with or attached to the intranasal mucosa modify allergen receptors on the intranasal mucosa, inhibiting antigen-antibody reactions on the intranasal mucosa, and that this is involved in the prevention effect of the composite-particles-attached sheet on allergic rhinitis.

Test Example 6

Treatment Effect of Composite-Particles-Attached Sheet on Allergic Rhinitis

In this Test Example, the composite-particles-attached sheet manufactured in Manufacturing Example 3 was evaluated for treatment effect on allergic rhinitis. The following tests were carried out for each test subject.

[Test A-6]

From start of cleaning to occurrence of the three main symptoms: the test subjects each started cleaning with nothing inserted into their nasal cavity. The three main symptoms occurred to each test subject 10 to 30 minutes after start of cleaning.

From occurrence of the three main symptoms to finish of cleaning: the test subjects each finished cleaning 40 minutes after occurrence of the three main symptoms.

From finish of cleaning to 12 hours after finish of cleaning: the test subjects each with nothing inserted into their nasal cavity were evaluated for the three main symptoms of allergic rhinitis.

[Test B-6]

From start of cleaning to occurrence of the three main symptoms: the test subjects each started cleaning with nothing inserted into their nasal cavity. The three main symptoms occurred to each test subject 10 to 30 minutes after start of cleaning.

From occurrence of the three main symptoms to finish of cleaning: 10 minutes after occurrence of the three main symptoms, the test subjects each inserted the same nonwoven fabric (not containing composite particles) as was used to manufacture composite-particles-attached sheets into the back in the nasal cavity (inferior nasal concha) (about 1 to 8 cm from the subnasal point), and finished cleaning 40 minutes after occurrence of the three main symptoms. They put off the nonwoven fabrics when they finished cleaning.

From finish of cleaning to 12 hours after finish of cleaning: the test subjects each with nothing inserted into their nasal cavity were evaluated for the three main symptoms of allergic rhinitis.

[Test C-6]

From start of cleaning to occurrence of the three main symptoms: the test subjects each started cleaning with nothing inserted into their nasal cavity. The three main symptoms occurred to each test subject 10 to 30 minutes after start of cleaning.

From occurrence of the three main symptoms to finish of cleaning: 10 minutes after occurrence of the three main symptoms, the test subjects each inserted the composite-particles-attached sheet into the back in the nasal cavity (inferior nasal concha) (about 1 to 8 cm from the subnasal point), and finished cleaning 40 minutes after occurrence of the three main symptoms. They put off the composite-particles-attached sheets when they finished cleaning.

From finish of cleaning to 12 hours after finish of cleaning: the test subjects each with nothing inserted into their nasal cavity were evaluated for the three main symptoms of allergic rhinitis.

The following items apply to each test.

When Test A-6, Test B-6, and Test C-6 were carried out to the same test subject, an interval of three days or more between Tests was allowed.

The start time of cleaning was 10 o'clock in the morning.

The cleaning items included the cleaning of an about eight-Japanese-tatami-mat bedroom using a vacuum cleaner, the putting-down/away of Japanese futon, the arrangement of books, and the wiping of a table top.

Evaluation of the three main symptoms was carried out with the aforementioned changes made to the evaluation criteria of the Practical Guideline for the Management of Allergic Rhinitis in Japan 2016 (the eighth revision) (written by the Committee of the Practical Guideline for the Management of Allergic Rhinitis in Japan, and published by Life Science Co., Ltd.)

The results of Test A-6, Test B-6, and Test C-6 are shown in Table 10.

TABLE 10

Results of Test A-6, Test B-6, and Test C-6

| Symptom | Test | Patient No. 1 | 2 | 3 | 4 | 5 | 6 | Average Score |
|---|---|---|---|---|---|---|---|---|
| Paroxysmal sneeze | Test A-6 | 3 | 4 | 4 | 4 | 3 | 3 | 3.5 |
|  | Test B-6 | 3 | 4 | 4 | 4 | 3 | 3 | 3.5 |
|  | Test C-6 | 0 | 0 | 0 | 0 | 0 | 0 | 0.0 |
| Nasal discharge | Test A-6 | 3 | 4 | 4 | 4 | 3 | 4 | 3.7 |
|  | Test B-6 | 3 | 4 | 3 | 4 | 3 | 4 | 3.5 |
|  | Test C-6 | 2 | 1 | 0 | 0 | 1 | 0 | 0.7 |
| Nasal congestion | Test A-6 | 3 | 4 | 3 | 4 | 3 | 3 | 3.3 |
|  | Test B-6 | 3 | 4 | 3 | 4 | 3 | 3 | 3.3 |
|  | Test C-6 | 0 | 0 | 1 | 1 | 0 | 0 | 0.3 |

In Test C-6 in which the composite-particles-attached sheets were used, the persistence of the three main symptoms of allergic rhinitis in each test subject was inhibited with a significant difference, compared to Test A-6 in which no nonwoven fabrics were used and Test B-6 in which normal nonwoven fabrics (not containing composite particles) were used. In addition, the effect of inhibiting the three main symptoms of allergic rhinitis from occurring was maintained for a few hours to several days after the composite-particles-attached sheets were put off, although there were differences between individual test subjects.

This has revealed that the composite-particles-attached sheet has the effect of treating allergic rhinitis.

It is considered that either or both the composite particles present on the parts of the composite-particles-attached sheet which are in contact with the intranasal mucosa or/and the composite particles which are detached from the composite-particles-attached sheet by the breathing of each test subject and attached to the intranasal mucosa inactivate (decompose) allergens (antigen proteins), such as house dust, mites, mold, and pollen, on the intranasal mucosa and inhibit antigen-antibody reactions on the intranasal mucosa, thereby exerting the treatment effect of the composite-particles-attached sheet on allergic rhinitis.

Although there were differences between individual test subjects, the fact that the effect of inhibiting the three main symptoms of allergic rhinitis from occurring was maintained for a few hours to several days after the composite-particles-attached sheet was put off suggests that the inactivation (decomposition) of allergens (antigen proteins) on the intranasal mucosa is not necessarily all involved in the treatment effect of the composite-particles-attached sheet on allergic rhinitis.

There is considered to be a possibility that the composite particles which have been put into contact with or attached to the intranasal mucosa modify allergen receptors on the intranasal mucosa, inhibiting antigen-antibody reactions on the intranasal mucosa, and that this is involved in the treatment effect of the composite-particles-attached sheet on allergic rhinitis.

Test Example 7

Specimens S1 to S3 having a size of 1 cm×5 cm were made of the polyester-made spunlaced nonwoven fabric ("S0040" made by Yuho Co., Ltd., the amount of mass per unit area: 40 g/m$^2$) for which the total attached amount (total fixed amount) of composite particles M1 and binder resin was adjusted to 4 g/m$^2$, as was manufactured in the same manner as in Manufacturing Example 2.

The specimens S1 to S3 were heat-treated at 160° C. for 5 minutes, added to 30 mL of physiological saline, and allowed to stand in a thermostatic chamber at 37° C. for 2 hours. After the nonwoven fabric was removed from the physiological saline, the physiological saline was filtered through a membrane filter (pore size: 0.1 µm).

The titanium ions and silver ions included in the filtrate were quantified with the plasma spectrometry device ("Agilent 7800" from Agilent Technologies Japan, Ltd.). In addition, a specimen without being added to 30 mL of physiological saline was quantified in the same manner as above, and used as a control. Each specimen was quantified three times, and the average value of the three quantitative values was determined. The minimum limit of detection was 1.0 ppb. The quantification results are shown in Table 11 and Table 12.

TABLE 11

Quantification Results of Titanium Ions in Filtrate (Unit: ppb)

|  |  | Control | Test Specimen | | |
|---|---|---|---|---|---|
|  |  |  | S1 | S2 | S3 |
| Quantitative value | First | <1.0 | <1.0 | <1.0 | <1.0 |
|  | Second | <1.0 | <1.0 | <1.0 | <1.0 |
|  | Third | <1.0 | <1.0 | <1.0 | <1.0 |
|  | Average value | <1.0 | <1.0 | <1.0 | <1.0 |

TABLE 12

Quantification Results of Silver Ions in Filtrate (Unit: ppb)

|  |  | Control | Test Specimen | | |
|---|---|---|---|---|---|
|  |  |  | S1 | S2 | S3 |
| Quantitative value | First | <1.0 | 3.6 | 2.1 | 4.0 |
|  | Second | <1.0 | 3.6 | 2.0 | 4.0 |
|  | Third | <1.0 | 3.6 | 2.0 | 3.8 |
|  | Average value | <1.0 | 3.6 | 2.0 | 3.9 |

The membrane filter resulting after the filtration was dissolved by a liquid mixture of hydrofluoric acid and nitric acid, and microwave-treated, whereafter the titanium element and the silver element included in the dissolution liquid were quantified with the plasma emission spectrometry device ("PS3520UVDDII" from Hitachi High-Tech Science Corporation). In addition, a specimen without being added to 30 mL of physiological saline was quantified in the same manner as above, and used as a control. Each specimen was quantified three times, and the average value of the three quantitative values was determined. The minimum limit of detection was 1 µg. The quantification results are shown in Table 13 and Table 14.

TABLE 13

Quantification Results of Titanium Element (Unit: µg)

|  |  | Control | Test Specimen | | |
|---|---|---|---|---|---|
|  |  |  | S1 | S2 | S3 |
| Quantitative value | First | <1 | 1 | 1 | <1 |
|  | Second | <1 | 1 | 1 | <1 |
|  | Third | <1 | 1 | 1 | <1 |
|  | Average value | <1 | 1 | 1 | <1 |

TABLE 14

Quantification Results of Silver Element (Unit: µg)

|  |  | Control | Test Specimen | | |
|---|---|---|---|---|---|
|  |  |  | S1 | S2 | S3 |
| Quantitative value | First | <1 | <1 | <1 | <1 |
|  | Second | <1 | <1 | <1 | <1 |
|  | Third | <1 | <1 | <1 | <1 |
|  | Average value | <1 | <1 | <1 | <1 |

In that the calculated values of the attached ingredient amounts in one specimen (size: 1 cm×5 cm) are 1.13×10$^{-3}$ (g) of titanium oxide, 2.94×10$^{-4}$ (g) of hydroxyapatite, 7.55×10$^{-6}$ (g) of silver, and 5.71×10$^{-4}$ (g) of binder resin, the above results indicate that although the specimen was immersed in physiological saline, most of the titanium oxide and silver remained in the nonwoven fabric. Accordingly, it is considered that even though a patient having the composite-particles-attached sheet inserted into the nasal cavity of the patient develops a runny nose, most of the composite particles remain in the sheet without eluting out or falling off, and hence that the composite-particles-attached sheet can exert the effect of preventing or treating rhinitis in a sustained manner.

Test Example 8

A specimen S4 having a size of 1 cm×5 cm was made of the polyester-made spunlaced nonwoven fabric ("S0040" from Yuho Co., Ltd., the amount of mass per unit area: 40 g/m$^2$) for which the total attached amount (total fixed amount) of composite particles M1 and binder resin was adjusted to 4 g/m$^2$, as was manufactured in the same manner as in Manufacturing Example 2.

The specimen S4 was heat-treated at 160° C. for 5 minutes, added to 30 mL of physiological saline, and allowed to stand in a thermostatic chamber at 37° C. for 2 hours. After the nonwoven fabric was removed from the physiological saline, the physiological saline was filtered through a membrane filter (pore size: 0.1 µm).

The membrane filter resulting after the filtration was observed with a scanning electron microscope (SEM). In addition, a specimen without being added to 30 mL of physiological saline was observed in the same manner as above, and used as a control.

Results of the SEM observation are shown in FIGS. 8 to 13.

Figure 8:
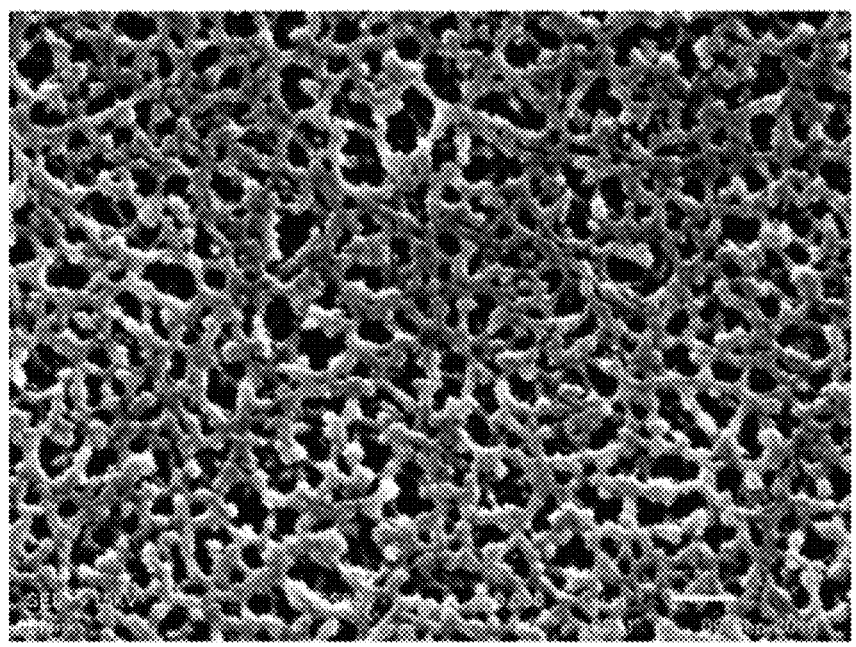
FIG. 8 is a view illustrating a result of the electron microscopic observation (10000× magnification) in Test Example 8.

FIG. 8 shows an SEM observation result (10000× magnification) for the control. As shown in FIG. 8, particles were not observed on the membrane filter in the control.

FIG. 9 to FIG. 13 show results of the SEM observation (3000× or 5000× magnification) of the particles captured by the membrane filter. As shown in FIG. 9 to FIG. 13, in a case in which the composite-particles-attached nonwoven fabric was immersed in physiological saline, the particles were observed on the membrane filter. The scale bars in FIGS. 9 to 13 represent 5 µm.

Figure 9:
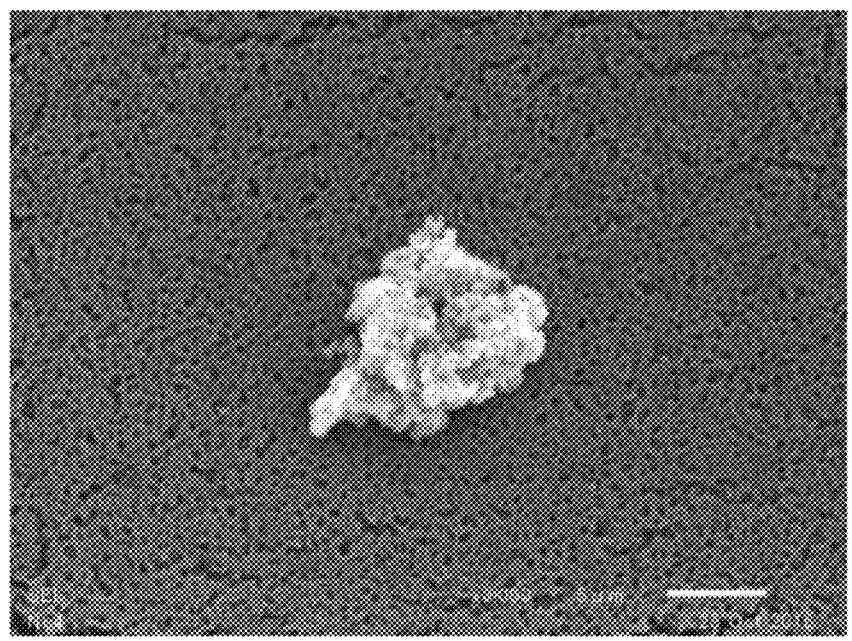
FIG. 9 is a view illustrating a result of the electron microscopic observation (3000× magnification) in Test Example 8.
Figure 10:
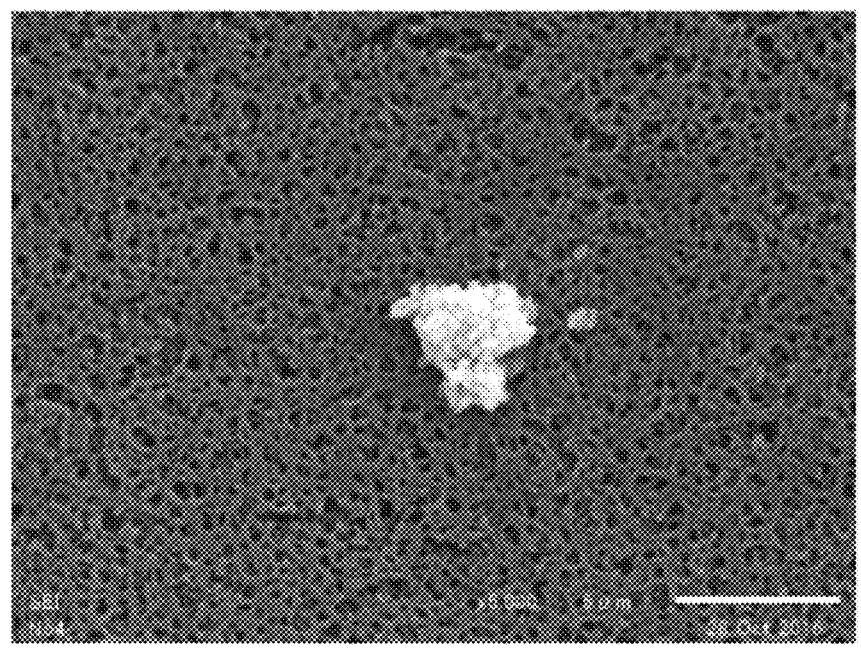
FIG. 10 is a view illustrating a result of the electron microscopic observation (5000× magnification) in Test Example 8.
Figure 11:
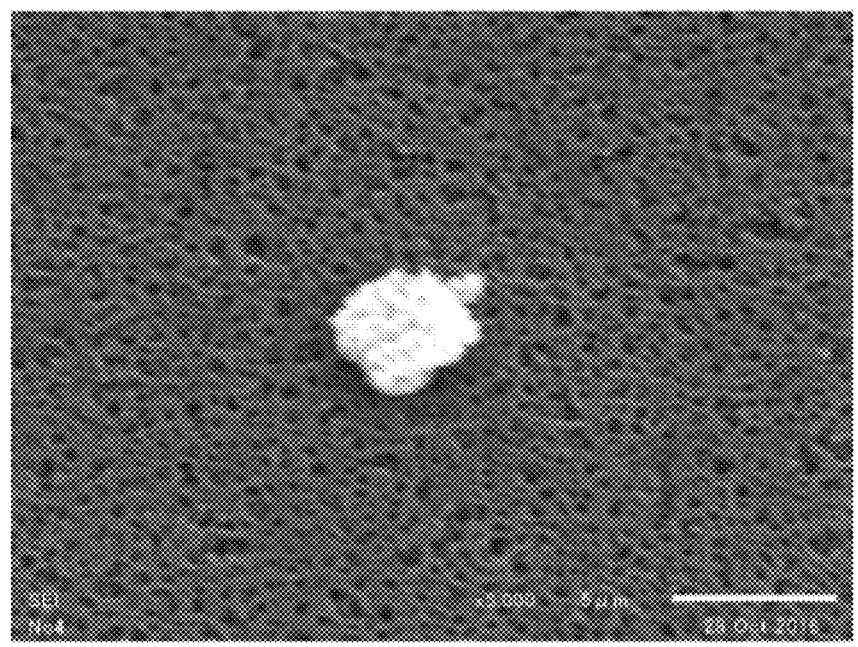
FIG. 11 is a view illustrating a result of the electron microscopic observation (5000× magnification) in Test Example 8.
Figure 12:
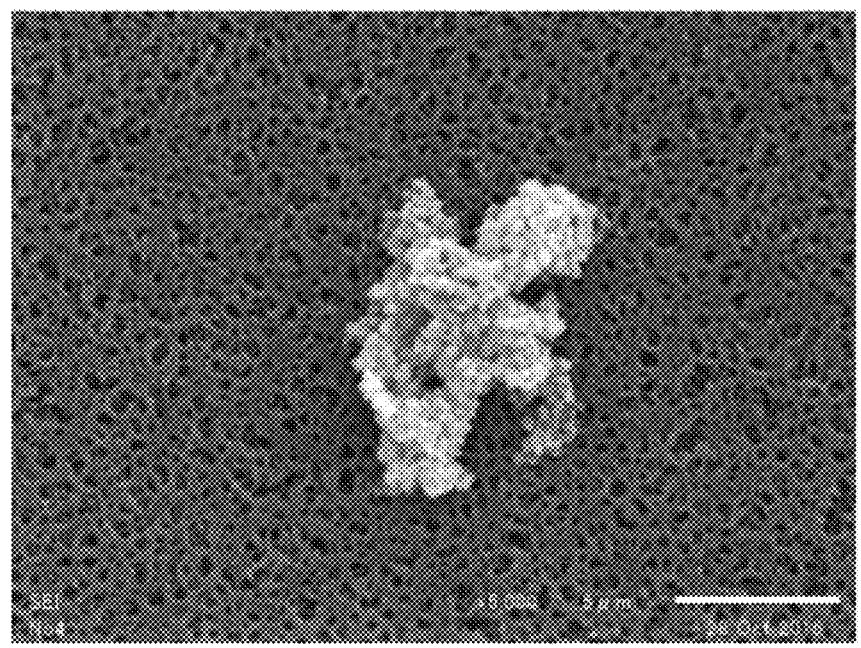
FIG. 12 is a view illustrating a result of the electron microscopic observation (5000× magnification) in Test Example 8.
Figure 13:
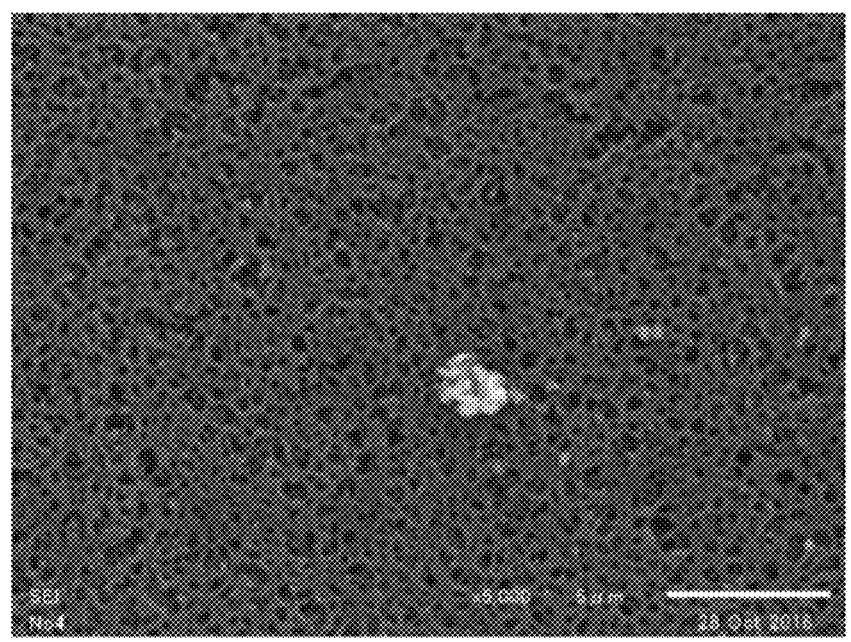
FIG. 13 is a view illustrating a result of the electron microscopic observation (5000× magnification) in Test Example 8.

With respect to the particles shown in FIG. 9 and FIG. 12, an energy-dispersive X-ray spectrometer (EDS) was used to carry out the element mapping (X-ray mapping) of the Ti element, Ag element, P element, and Ca element by characteristic X-ray and to analyze the distribution of each element.

Figure 14:
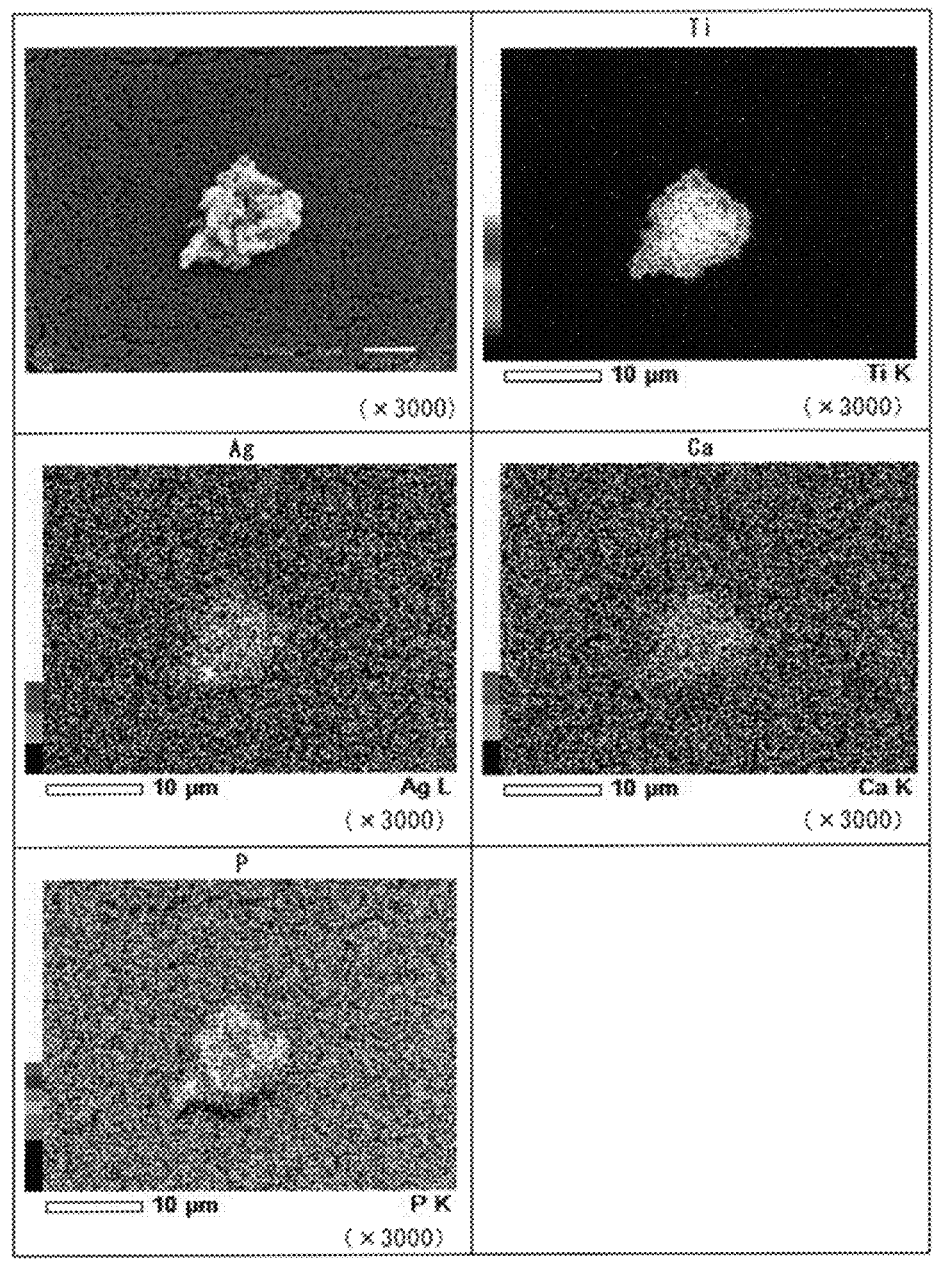
FIG. 14 is a view illustrating results of the element mapping (X-ray mapping) in Test Example 8.
Figure 15:
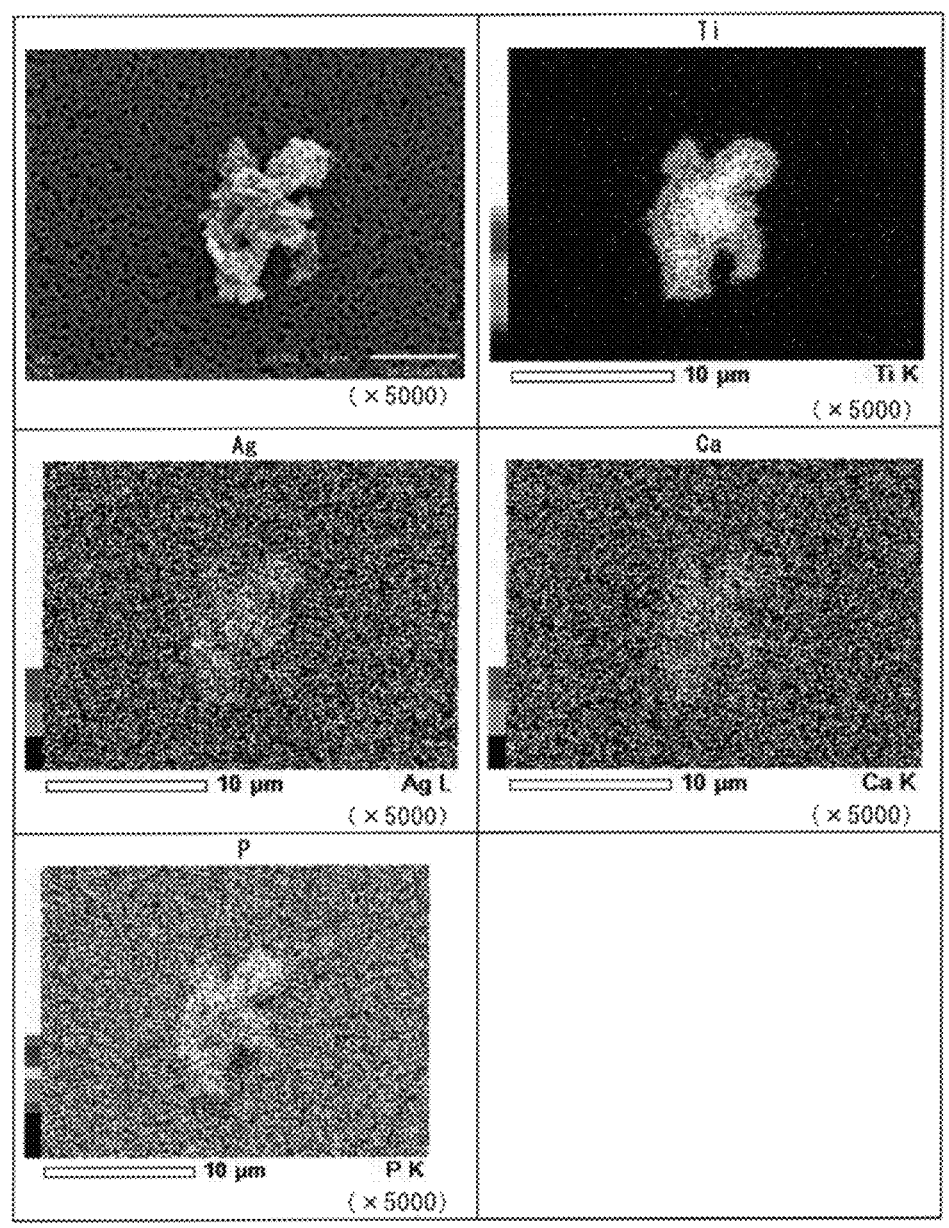
FIG. 15 is a view illustrating results of the element mapping (X-ray mapping) in Test Example 8.

Analysis results are shown in FIG. 14 and FIG. 15.

FIG. 14 shows analysis results of the element mapping for the particles shown in FIG. 9, and FIG. 15 shows analysis results of the element mapping for the particles shown in FIG. 12. As shown in FIG. 14 and FIG. 15, it is ascertained that the Ti element, Ag element, P element, and Ca element distribute all over the particles. This confirms that composite particles including one or more titanium oxide particles, one or more silver particles, and one or more hydroxyapatite particles are included in the composite particle M1.

Test Example 9

The composite-particles-attached mask manufactured in Manufacturing Example 4 was cut to manufacture a specimen 47 mm in diameter. The specimen was hold such that the side of the mask which faced the external air if put on a person's face was the upper side and the side of the mask which faced the person's face if put on was the lower side, and the upper and lower sides were pinched by two polyethylene-made ring-shaped holders (47 mm in outside diameter, 20 mm in inside diameter). A flow meter and a suction pump were connected to the lower side holder via piping, and a preliminary suction was carried out (at 5 L/minute for about 10 seconds). After the preliminary suction, a trapping filter (MF-MILLIPORE VCWP09025, 90 mm in diameter) was connected between the lower side holder and the flow meter/suction pump via piping, and a main suction was carried out (at 10 L/minute for 8 hours). This trapping filter can trap particles having a particle size of 0.1 µm or more. For piping, a pipe which was washed by sonication in pure water for 3 minutes and dried was used. The pressure (negative pressure) between the lower side spacer and the trapping filter was measured with the digital manometer (HT-1500NH made byHodaka Corp.).

After the main suction, the holder and the pipe were washed with about 40 mL of pure water, and solids in the wash liquid were trapped by the trapping filter (MF-MILLIPORE VCWP04700, 47 mm in diameter).

The trapping filter 90 mm in diameter and the trapping filter 47 mm in diameter were dissolved by a mixed acid solution of hydrofluoric acid and nitric acid, and microwave-treated, whereafter the titanium, silver, and hydroxyapatite included in the dissolution liquid were quantified with the plasma emission spectrometry device ("PS3520UVDDII" made by Hitachi High-Tech Science Corporation).

A composite-particles-attached mask was manufactured in the same manner as in Manufacturing Example 4, except that the composite-particles-attached nonwoven fabric N1 in which the total attached amount (total fixed amount) of composite particles M1 and binder resin was 4 g/m$^2$, 6 g/m$^2$, 8 g/m$^2$, or 10 g/m$^2$ was used in place of the composite-particles-attached nonwoven fabric N2 in which the total attached amount (total fixed amount) of composite particles M2 and binder resin was 13.5 g/m$^2$. The manufactured composite-particles-attached mask was cut to manufacture a specimen 47 mm in diameter, and tested in the same manner as described above. However, another test was carried out in which polyethylene-made ring-shaped holders (47 mm in outside diameter, 39 mm in inside diameter) were used in place of the polyethylene-made ring-shaped holders (47 mm in outside diameter, 20 mm in inside diameter) as two holders pinching the upper and lower sides of the specimen. In addition, another test was carried out in which a main suction was carried out without a preliminary suction.

The results are shown in Table 15.

TABLE 15

| Conditions and Results of Suction Test | | | | | | |
|---|---|---|---|---|---|---|
| Total Attached Amount (g) | Preliminary suction | Inside Diameter of Holder (mm) | Negative Pressure (mmHg) | Titanium Oxide (g) | Silver (g) | Hydroxyapatite (g) |
| 13.5 | Yes | 20 | 4.5 to 5.1 | $6.92 \times 10^{-4}$ | $2.39 \times 10^{-5}$ | $7.95 \times 10^{-5}$ |
| 10 | No | 39 | 0.8 to 0.9 | $6.82 \times 10^{-3}$ | $4.32 \times 10^{-5}$ | $1.71 \times 10^{-3}$ |
| 8 | Yes | 20 | 5.4 to 6.6 | $4.81 \times 10^{-4}$ | $3.07 \times 10^{-6}$ | $1.21 \times 10^{-4}$ |
| 4 | Yes | 20 | 5.0 to 6.4 | $2.41 \times 10^{-4}$ | $1.48 \times 10^{-6}$ | $6.05 \times 10^{-5}$ |
| 4 | No | 20 | 5.2 to 6.9 | $2.41 \times 10^{-4}$ | $1.48 \times 10^{-6}$ | $6.05 \times 10^{-5}$ |
| 4 | No | 39 | 0.5 | $2.72 \times 10^{-3}$ | $1.68 \times 10^{-5}$ | $6.93 \times 10^{-4}$ |

As shown in Table 15, composite particles were detached from the composite-particles-attached nonwoven fabric by suction. Accordingly, it is considered that when the subject wearing the composite-particles-attached mask breathes, part of the numerous composite particles attached to the mask are detached and taken into the nasal cavity of the subject. In other words, it is considered that utilizing the breathing of a subject wearing the composite-particles-attached mask enables the composite particles to be administered to the intranasal mucosa of the subject, thereby enabling the prevention or treatment of rhinitis of the subject.

Test Example 10

In this Test Example, the composite-particles-attached nonwoven fabric manufactured in Manufacturing Example 2 was cut to manufacture a reed-shaped composite-particles-attached sheet 2 cm in width and 15 cm in length, and this composite-particles-attached sheet was evaluated for prevention and treatment effects of allergic rhinitis. As a composite-particles-attached nonwoven fabric, the composite-particles-attached nonwoven fabric N1 which was manufactured in Manufacturing Example 2 and in which the total attached amount (total fixed amount) of composite particles M1 and binder resin was 4 g/m$^2$ was used.

(1) Test Subjects

As candidates for test subjects in this test, the patients with allergic rhinitis were selected who experienced sneezing, nasal discharge, and nasal congestion substantially every day in the March to May period which is the season for pollinosis, whose pollinosis score was 3 to 4 as diagnosed by an otolaryngologic specialist on the basis of the diagnostic criteria of the Practical Guideline for the Management of Allergic Rhinitis in Japan 2013 of the Japanese Society of Allergology, and whose period of illness was 3 years or more. As test subjects of this test, 12 persons of 5 males and 7 females, 28 to 54 years old, were selected with their consent from patients who were not able to obtain a certain clinical effect from conventional drug therapies and were resistant to therapy. The average age of the test subjects in this test was 47.6. The detailed characteristics of the test subjects are shown below.

[Test Subject No. 1]

Test Subject No. 1 is a 26 years old female, has contracted pollinosis and perennial allergy every year since 18 years ago which present the symptoms of sneezing, nasal discharge, and nasal congestion, and has used standard medical agents up to now. The medical agents (antihistaminic agent, intranasal steroid nebulization, and the like) which have been used hitherto alleviate the symptoms, but none of them have exhibited satisfactory effects nor persisting treatment effects.

[Test Subject No. 2]

Test subject No. 2 is a 33 years old female, has had the pollinosis allergic symptoms of sneezing, nasal discharge, and nasal congestion every year continuously since she was about 6 years old, has continued to use standard medical agents, but has obtained satisfactory effects from none of them, and has had a severe symptom of nasal discharge in particular, having trouble in daily life in the pollinosis season.

[Test Subject No. 3]

Test Subject No. 3 is a 34 years old female and has had pollinosis complicated by metal allergy in addition, which occurred suddenly 4 years ago. She exhibits the characteristic symptoms of sneezing, nasal discharge, and nasal congestion and has tried a lot of standard medical agents, but has not been able to take them continuously because she has exhibited a side effect of drowsiness. She had a nasal discharge running down to the pillow if only lying down on a bed, had no choice but to do mouth breathing because of her nasal congestion while sleeping, and has been in the state of a severe sleeplessness symptom.

[Test Subject No. 4]

Test subject No. 4 is a 38 years old female, has had the pollinosis allergic symptoms of sneezing, nasal discharge, and nasal congestion every year continuously since she was about 7 years old, has continued to use standard medical agents, but has obtained satisfactory effects from none of them, having trouble in daily life.

[Test Subject No. 5]

Test Subject No. 5 is a 44 years old female, had her pollinotic symptoms exacerbated when she was about 32 years old, has had symptomatic treatment by taking medicine when having severe symptoms, but has not had sufficient treatment effects.

[Test Subject No. 6]

Test Subject No. 6 is a 44 years old female, had her pollinotic symptoms exacerbated when she was about 28 years old, had a cauterization by laser on her intranasal mucosa twice in the past only to have no complete response, has had symptomatic treatment by taking medicine when having severe symptoms, but has not had sufficient treatment effects.

[Test Subject No. 7]

Test subject No. 7 is a 45 years old male, has had the pollinosis allergic symptoms of sneezing, nasal discharge, and nasal congestion every year continuously since about 5 years ago, has continued to use standard medical agents, but has obtained satisfactory effects from none of them, and has been in the state in which he has severe symptoms of nasal discharge and sneezing in particular, every morning.

[Test Subject No. 8]

Test subject No. 8 is a 47 years old male, has had the pollinosis allergic symptoms of sneezing, nasal discharge, and nasal congestion every year continuously since he was about 22 years old, and has continued to use standard medical agents. He had a laser therapy once in 2015, but the effect was incomplete, and hence he takes antihistaminic agents when necessary.

[Test Subject No. 9]

Test Subject No. 9 is a 49 years old male, has contracted pollinosis and perennial allergy since 18 years ago which develop the symptoms of sneezing, nasal discharge, and nasal congestion, and has used standard medical agents up to now. The medical agents (antihistaminic agents, antileukotriene agents, vasoconstrictors, intranasal steroid sprays, steroid oral medicines, various Chinese herbal medicines, and the like) which have been used hitherto alleviate the symptoms, but none of them have exhibited satisfactory effects nor persisting treatment effects.

[Test Subject No. 10]

Test subject No. 10 is a 50 years old male, has had the pollinosis allergic symptoms of sneezing, nasal discharge, and nasal congestion every year continuously since 40 years ago, has continued to use standard medical agents, but has obtained satisfactory effects from none of them, has had severe nasal congestion in particular, because of which he has used vasoconstrictors and the like, but has had a tendency for the symptoms to worsen year by year, having trouble in daily life.

[Test Subject No. 11]

Test subject No. 11 is a 50 years old female, has had pollinotic symptoms exacerbated since she was about 28 years old, has continued to use standard medical agents, but has obtained satisfactory effects from none of them.

[Test Subject No. 12]

Test Subject No. 12 is a 53 years old male, has contracted pollinosis as well as perennial allergy since 40 years ago which develops the symptoms of sneezing, nasal discharge, and nasal congestion, has used standard medical agents for years, but has obtained satisfactory effects from none of them.

(2) Evaluation Index

As an index for evaluating the clinical prevention and treatment effects of the composite-particles-attached sheet on allergic rhinitis, the three main symptoms of sneezing, nasal discharge, and nasal congestion were scored on the basis of the Practical Guideline for the Management of Allergic Rhinitis in Japan presented by the Japanese Society of Allergology in 2013. Clinical symptoms of the three main symptoms were written on recording paper as self-reported at the time of awakening. For the three main symptoms of sneezing, nasal discharge, and nasal congestion, 0 points to "none", 1 point to "light", 2 points to "a little severe", 3 points to "severe", and 4 points to "very severe" were given, and the Total Symptom Score (TSS) for evaluating the overall effects was calculated as the total of scores for the three main symptoms.

(3) Evaluation Method

In order to evaluate the true clinical prevention and treatment effects of the composite-particles-attached sheet, placebo effects need to be eliminated. Each test subject wore a normal mask for two days, then had a normal nonwoven fabric sheet with no composite particle attached inserted into the nasal cavity for five days, and then had a composite-particles-attached sheet inserted into the nasal cavity for five days. The normal nonwoven fabric sheet with no composite particle attached (2 cm in width, 15 cm in length) was made a twisted paper string and inserted into the nasal cavity of each test subject (about 1 to 8 cm from the subnasal point) for 40 minutes from 9 o'clock in the morning for 5 days in a row. The composite-particles-attached sheet (2 cm in width, 15 cm in length) was made a twisted paper string and inserted into the nasal cavity of each test subject (about 1 to 8 cm from the subnasal point) for 40 minutes from 9 o'clock in the morning for 5 days in a row. The test subjects themselves inserted the sheet into their nasal cavity.

Each test subject self-evaluated their three main symptoms of sneezing, nasal discharge, and nasal congestion every day for 5 days. In that there was almost no change in the three main symptoms between when the normal mask was used for 2 days and when the normal nonwoven fabric sheet with no composite particle attached was used for 5 days, the average value of scores for the 2 days when the normal mask was used and the average value of scores for the 5 days when the normal nonwoven fabric sheet with no composite particle attached was used were determined and compared with the scores for the 5 days (each day from the first day to the fifth day) when the composite-particles-attached sheet was used, to thereby compare and verify the subjective clinical prevention effect of the three main symptoms statistically, using a paired t-test. The statistical significance level of the test was 0.1%.

For the average value of scores for the 5 days when the normal nonwoven fabric sheet with no composite particle attached was used and for the scores for the 5 days (score for each day from the first day to the fifth day) when the composite-particles-attached sheet was used, a paired t-test was carried out relative to the average value of scores for the 2 days when the normal mask was used as a control, and for comparison by groups, a statistical test was carried out by analysis based on one-way analysis of variance after a test of homogeneity of variance.

For ethical consideration, the Declaration of Helsinki was observed. When the necessity of stopping the use of the composite-particles-attached sheet was recognized, the test subjects were allowed to stop the use if appropriate on their own judgement. The test subjects were informed that the stopping was based on their free-will and would not give them any disadvantages, and were asked for continued cooperation. One of the 12 persons showed a case in which the use of the composite-particles-attached sheet exhibited some effect but the person had a feeling of discomfort on the mucosa from the fourth day on and could not do clinical self-evaluation.

(4) Results

The scores (sneezing score, nasal discharge score, nasal congestion score, and overall symptom score) for the case in which the normal mask was used for 2 days, for the case in which the normal nonwoven fabric sheet with no composite particle attached was used for five days, and for the case in which the composite-particles-attached sheet was used for 5 days are each shown in Table 16. The statistical test results are shown in Table 17.

TABLE 16

| Score | Treatment | | Degree | Minimum Value | Maximum Value | Average Value | Standard Deviation |
|---|---|---|---|---|---|---|---|
| Sneezing score | Normal mask | | 12 | 0.00 | 4.00 | 2.25 | 1.12 |
| | Normal nonwoven fabric sheet | | 12 | 0.00 | 4.00 | 2.33 | 1.11 |
| | Composite-particles-attached sheet | 1st day | 12 | 0.00 | 3.00 | 1.42 | 1.00 |
| | | 2nd day | 12 | 0.00 | 3.00 | 1.42 | 1.08 |
| | | 3rd day | 12 | 0.00 | 2.00 | 1.00 | 0.60 |
| | | 4th day | 12 | 0.00 | 2.00 | 0.83 | 0.72 |
| | | 5th day | 11 | 0.00 | 2.00 | 0.73 | 0.65 |
| Nasal discharge score | Normal mask | | 12 | 2.00 | 4.00 | 3.08 | 0.79 |
| | Normal nonwoven fabric sheet | | 12 | 1.60 | 4.00 | 3.03 | 0.95 |
| | Composite-particles-attached sheet | 1st day | 12 | 1.00 | 4.00 | 2.12 | 0.94 |
| | | 2nd day | 12 | 1.00 | 3.00 | 1.92 | 0.79 |
| | | 3rd day | 12 | 0.00 | 3.00 | 1.50 | 0.90 |
| | | 4th day | 11 | 0.00 | 3.00 | 1.45 | 1.04 |
| | | 5th day | 11 | 0.00 | 3.00 | 1.36 | 1.03 |
| Nasal congestion score | Normal mask | | 12 | 2.00 | 4.00 | 3.08 | 0.79 |
| | Normal nonwoven fabric sheet | | 12 | 1.00 | 4.00 | 3.05 | 0.84 |
| | Composite-particles-attached sheet | 1st day | 12 | 1.00 | 3.00 | 2.00 | 0.85 |
| | | 2nd day | 12 | 0.00 | 3.00 | 1.83 | 0.83 |
| | | 3rd day | 12 | 0.00 | 3.00 | 1.33 | 0.89 |
| | | 4th day | 11 | 0.00 | 2.00 | 1.09 | 0.70 |
| | | 5th day | 11 | 0.00 | 3.00 | 0.82 | 1.08 |
| Overall symptom score | Normal mask | | 12 | 6.00 | 12.00 | 8.46 | 2.22 |
| | Normal nonwoven fabric sheet | | 12 | 5.00 | 11.80 | 8.42 | 2.12 |
| | Composite-particles-attached sheet | 1st day | 12 | 3.00 | 9.00 | 5.50 | 1.93 |
| | | 2nd day | 12 | 3.00 | 9.00 | 6.17 | 1.90 |
| | | 3rd day | 12 | 2.00 | 9.00 | 5.17 | 1.75 |
| | | 4th day | 11 | 1.00 | 8.00 | 5.00 | 1.84 |
| | | 5th day | 11 | 1.00 | 9.00 | 4.55 | 2.30 |

TABLE 17

Statistical Test Results

Difference of Corresponding Sample(A-B)

| Score | A | B | | Average Value | Standard Deviation | Standard error of average value | 95% confidence interval of difference Upper Limit | 95% confidence interval of difference Lower Limit | t-value | degree of Freedom | Significance Probability (both sides) |
|---|---|---|---|---|---|---|---|---|---|---|---|
| Sneezing score | Average of normal mask | Average value of normal nonwoven fabric sheet | | −0.08333 | 0.46482 | 0.13418 | −0.37867 | 0.21200 | −0.621 | 11 | 0.547 |
| | | Composite-particles-attached-sheet | 1st day score | 0.83333 | 0.68534 | 0.19784 | 0.39789 | 1.26878 | 4.212 | 11 | 0.001 |
| | | | 2nd day score | 0.83333 | 0.96138 | 0.27753 | 0.22250 | 1.44416 | 3.003 | 11 | 0.012 |
| | | | 3rd day score | 1.25000 | 1.11803 | 0.32275 | 0.53964 | 1.96036 | 3.873 | 11 | 0.003 |
| | | | 4th day score | 1.41667 | 1.22165 | 0.35266 | 0.64047 | 2.19286 | 4.017 | 11 | 0.002 |
| | | | 5th day score | 1.63636 | 1.09752 | 0.33091 | 0.89904 | 2.37369 | 4.945 | 10 | 0.001 |
| Sneezing score | Average of normal mask | Average value of normal nonwoven fabric sheet | | 0.05000 | 0.29695 | 0.08572 | −0.13868 | 0.23868 | 0.583 | 11 | 0.571 |
| | | Composite-particles-attached-sheet | 1st day score | 0.91667 | 1.12479 | 0.32470 | 0.20201 | 1.63132 | 2.823 | 11 | 0.017 |
| | | | 2nd day score | 1.16667 | 1.11464 | 0.32177 | 0.45846 | 1.87488 | 3.626 | 11 | 0.004 |
| | | | 3rd day score | 1.58333 | 1.34559 | 0.38844 | 0.72839 | 2.43828 | 4.076 | 11 | 0.002 |
| | | | 4th day score | 1.54545 | 1.33144 | 0.40144 | 0.65098 | 2.43993 | 3.850 | 10 | 0.003 |
| | | | 5th day score | 1.63636 | 1.20605 | 0.36364 | 0.82613 | 2.44660 | 4.500 | 10 | 0.001 |
| Sneezing score | Average of normal mask | Average value of normal nonwoven fabric sheet | | 0.03333 | 0.53144 | 0.15341 | −0.30433 | 0.37099 | 0.217 | 11 | 0.832 |
| | | Composite-particles-attached-sheet | 1st day score | 1.08333 | 0.66856 | 0.19300 | 0.65855 | 1.50811 | 5.613 | 11 | 0.000 |
| | | | 2nd day score | 1.25000 | 0.86603 | 0.25000 | 0.69975 | 1.80025 | 5.000 | 11 | 0.000 |
| | | | 3rd day score | 1.75000 | 1.05529 | 0.30464 | 1.07950 | 2.42050 | 5.745 | 11 | 0.000 |
| | | | 4th day score | 1.90909 | 1.04447 | 0.31492 | 1.20741 | 2.61077 | 6.062 | 10 | 0.000 |
| | | | 5th day score | 2.18182 | 1.32802 | 0.40041 | 1.28964 | 3.07399 | 5.449 | 10 | 0.000 |
| Overall symptom score | Average of normal mask | Average value of normal nonwoven fabric sheet | | 0.04167 | 1.34736 | 0.38895 | −0.81440 | 0.89774 | 0.107 | 11 | 0.917 |
| | | Composite-particles-attached-sheet | 1st day score | 2.95833 | 2.25084 | 0.64976 | 1.52822 | 4.38845 | 4.553 | 11 | 0.001 |
| | | | 2nd day score | 2.29167 | 1.67139 | 0.48249 | 1.22971 | 3.35362 | 4.750 | 11 | 0.001 |
| | | | 3rd day score | 3.29167 | 2.29087 | 0.66132 | 1.83611 | 4.74722 | 4.977 | 11 | 0.000 |
| | | | 4th day score | 3.40909 | 2.27836 | 0.68695 | 1.87847 | 4.93971 | 4.963 | 10 | 0.001 |
| | | | 5th day score | 3.86364 | 2.74855 | 0.82872 | 2.01713 | 5.71014 | 4.662 | 10 | 0.001 |

(5) Discussion

As shown in Table 16 and Table 17, no statistical significant difference was recognized about any score between the average value of scores in the case in which the normal mask was used for 2 days and the average value of scores in the case in which the normal nonwoven fabric sheet with no composite particle attached was used for five days.

Also as shown in Table 16 and Table 17, a statistical significant difference (P<0.05) was recognized in any combination between the average value of scores in the case in which the normal mask was used for 2 days and the score for each day from the first day to the fifth day in the case in which the composite-particles-attached sheet was used for 5 days.

These results indicate that inserting the composite-particles-attached sheet into the nasal cavity can significantly improve the three main symptoms of sneezing, nasal discharge, and nasal congestion, in other words, that the composite-particles-attached sheet has a significant prevention effect and treatment effect of allergic rhinitis.

(6) Side Effect

The side effect of the composite-particles-attached sheet was verified on the basis of the subjective symptoms and degree of hematological change of the test subjects. In this regard, the case in which the normal nonwoven fabric sheet with no composite particle attached was inserted was used as a control. As a result, a temporary increase in the amount of nasal discharge was observed in the cases of 7 persons 30 minutes after the sheet was inserted into the nasal cavity, in both the group which used the composite-particles-attached sheet and the group which used the normal nonwoven fabric sheet. In addition, sneezing was slightly intensified in the cases of 3 persons. No other subjective side effects such as pain, epiphora, intensified nasal congestion, bleeding, smell disorder, feeling of numbness of the lips, and feeling of tingling in the nasal cavity were observed in any of the 12 cases. In addition, 6 persons were inspected for IgE and LDH in blood, which are immunological laboratory data, and no abnormal value was observed in any of the test subjects.

The invention claimed is:

1. A method for preventing or treating rhinitis in a subject in need thereof, the method comprising administering a composite particle to an intranasal mucosa of the subject,
    wherein the composite particle comprises at least one titanium oxide particle, at least one metal particle and at least one calcium phosphate particle,
    wherein the at least one metal particle is at least one metal particle selected from the group consisting of a silver particle, a gold particle, a platinum particle and a copper particle,
    wherein administering the composite particle to the intranasal mucosa of the subject comprises inserting a medical device into a nasal cavity of the subject,
    wherein the medical device comprises a sheet portion inserted into the nasal cavity of the subject and the composite particle attached to the sheet portion, and
    wherein the medical device is inserted into the nasal cavity of the subject so that the composite particle attached to the sheet portion comes into contact with the intranasal mucosa of the subject, and so that a part of the medical device is inserted into the nasal cavity of the subject and the other part remains outside of the nasal cavity of the subject.

2. The method according to claim 1, wherein the rhinitis is allergic rhinitis.

3. The method according to claim 1, wherein, in the composite particle, the at least one titanium oxide particle, the at least one metal particle and the at least one calcium phosphate particle are arranged three-dimensionally and randomly.

4. The method according to claim 1, wherein at least one metal particle is fixedly attached to at least one titanium oxide particle.

5. The method according to claim 1, wherein the at least one metal particle is a silver particle, and the at least one calcium phosphate particle is a hydroxyapatite particle.

6. The method according to claim 1, wherein the sheet portion is breathable.

7. The method according to claim 1, wherein the composite particle is detachably attached to the sheet portion.

8. The method according to claim 1, wherein the composite particle is detachably attached to the sheet portion via a binder resin.

9. The method according to claim 8, wherein the amount of the binder resin is 20 to 90 parts by mass, relative to 100 parts by mass of the composite particle.

* * * * *